United States Patent
Kramer et al.

(10) Patent No.: US 10,473,592 B2
(45) Date of Patent: Nov. 12, 2019

(54) METHODS FOR ESTIMATING PHOTOSYNTHETIC CHARACTERISTICS IN PLANT CANOPIES AND SYSTEMS AND APPARATUS RELATED THERETO

(71) Applicant: Board of Trustees of Michigan State University, East Lansing, MI (US)

(72) Inventors: David Kramer, Okemos, MI (US); Jin Chen, Lexington, KY (US); Elisabeth Ostendorf, East Lansing, MI (US); Lei Xu, East Lansing, MI (US); Jeffrey Cruz, Okemos, MI (US); Jeremy J. Brodersen, Grand Rapids, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/569,570

(22) PCT Filed: Apr. 29, 2016

(86) PCT No.: PCT/US2016/030193
§ 371 (c)(1),
(2) Date: Oct. 26, 2017

(87) PCT Pub. No.: WO2016/176612
PCT Pub. Date: Nov. 3, 2016

(65) Prior Publication Data
US 2018/0313760 A1    Nov. 1, 2018

Related U.S. Application Data

(60) Provisional application No. 62/154,405, filed on Apr. 29, 2015.

(51) Int. Cl.
*G01N 21/64*    (2006.01)
*A01G 7/00*    (2006.01)
(Continued)

(52) U.S. Cl.
CPC ............... *G01N 21/6486* (2013.01)

(58) Field of Classification Search
CPC ............ G01N 21/6486; A01G 7/045
See application file for complete search history.

(56) References Cited

U.S. PATENT DOCUMENTS

| 4,650,336 A | 3/1987 | Moll |
| 4,942,303 A | 7/1990 | Kolber et al. |

(Continued)

FOREIGN PATENT DOCUMENTS

| DE | 19910436 A1 | 10/2000 |
| WO | 2010101460 A1 | 9/2010 |

(Continued)

OTHER PUBLICATIONS

Lenk et al., "Multispectral fluorescence and reflectance imaging at the leaf level and its possible applications," Journal of Experimental Botany, vol. 58, No. 4, pp. 807-814, 2007. Retrieved from Internet [Dec. 17, 2018]; Retrieved from url <doi:10.1093/jxb/erl207>. (Year: 2007).*

(Continued)

*Primary Examiner* — Yara B Green
(74) *Attorney, Agent, or Firm* — Westman, Champlin & Koehler, P.A.

(57) ABSTRACT

Methods of determining and characterizing photosynthesis in plant parts of one or more plants includes capturing a plurality of images of the plant parts of the one or more plants with a sensor are provided. Fluorescence of the plant parts of the one or more plants can be measured by storing a sensor image of observed fluorescence. Light absorbed by the plant parts of the one or more plants can be estimated by observing red and/or infrared reflectance of the plant parts. A characteristic of photosynthesis such as linear electron flow in plant parts of the one or more plants can be derived (Continued)

using the measured fluorescence of the plant parts, the reflectance and the light absorbed by the plant parts, and/or the three-dimensional model comprising the plant parts of the one or more plants. Related apparatus and systems are also provided.

33 Claims, 18 Drawing Sheets

(51) Int. Cl.
    *G01N 21/63* (2006.01)
    *G01N 21/84* (2006.01)

(56) References Cited

U.S. PATENT DOCUMENTS

| | | | |
|---|---|---|---|
| 5,130,545 A * | 7/1992 | Lussier | A01G 7/00 250/458.1 |
| 5,412,219 A | 5/1995 | Chappelle et al. | |
| 6,121,053 A | 9/2000 | Kolber et al. | |
| 6,563,122 B1 | 5/2003 | Ludeker et al. | |
| 6,624,887 B1 * | 9/2003 | Kramer | G01N 21/255 356/318 |
| 7,214,947 B2 | 5/2007 | Bueno et al. | |
| 7,857,993 B2 | 12/2010 | Dai et al. | |
| 8,302,346 B2 | 11/2012 | Hunt et al. | |
| 8,796,631 B2 | 8/2014 | Penumadu et al. | |
| 9,429,521 B2 | 8/2016 | Kramer et al. | |
| 2001/0030742 A1 | 10/2001 | Kramer et al. | |
| 2005/0072935 A1 * | 4/2005 | Lussier | G01N 21/6456 250/458.1 |
| 2005/0077476 A1 | 4/2005 | Poteet et al. | |
| 2005/0239044 A1 | 10/2005 | Seibert et al. | |
| 2006/0273258 A1 | 12/2006 | Kastalsky et al. | |
| 2007/0085010 A1 | 4/2007 | Letant et al. | |
| 2008/0128624 A1 | 6/2008 | Cooke et al. | |
| 2008/0144013 A1 | 6/2008 | Lanoue et al. | |
| 2008/0237470 A1 | 10/2008 | Loureiro et al. | |
| 2010/0068750 A1 | 3/2010 | Pogosjan et al. | |
| 2010/0270462 A1 | 10/2010 | Nelson et al. | |
| 2011/0091945 A1 | 4/2011 | Das et al. | |
| 2011/0101239 A1 * | 5/2011 | Woodhouse | G01S 7/4802 250/458.1 |
| 2011/0179706 A1 | 7/2011 | Hunt et al. | |
| 2012/0310540 A1 | 12/2012 | McDermitt et al. | |
| 2013/0256561 A1 | 10/2013 | Greenbaum et al. | |
| 2015/0204787 A1 | 7/2015 | Kramer et al. | |

FOREIGN PATENT DOCUMENTS

| | | |
|---|---|---|
| WO | 2013181433 A2 | 12/2013 |
| WO | 2013181433 A3 | 12/2013 |

OTHER PUBLICATIONS

International Preliminary Report on Patentability received for PCT Patent application No. PCT/US2013/043426, dated Dec. 11, 2014, 7 pages.
International Search Report and Written Opinion received for PCT Patent Application No. PCT/US2013/043426, dated Nov. 12, 2013, 8 pages.
Communication pursuant to Article 94(3) EPC received for EP Application 13796653.7, dated Sep. 29, 2016, 13 pages.
Communication under Rule 71(3) EPC received for EP Application 13796653.7, dated Apr. 4, 2017, 7 pages.
Communication under Rule 71(3) EPC received for EP Application 13796653.7, dated Sep. 19, 2017, 3 pages.
Decision to Grant received for European Patent Application No. 13796653.7, dated Sep. 9, 2017, 2 pages.
Extended EP Search Report received for EP Patent Application 13796653.7, dated Nov. 11, 2015, 11 pages.
Invitation to Pay Additional Fees and Partial Search Report received for PCT Application No. PCT/US2016/030193, dated Aug. 23, 2016, 7 pages.
International Search Report and Written Opinion received for PCT Application PCT/US2016/030193, dated Oct. 14, 2016, 19 pages.
Notice of Allowance received for U.S. Appl. No. 14/404,338, dated Jan. 21, 2016, 10 pages.
Office Action received for CA Application No. 2,874,853, dated Dec. 30, 2014, 4 pages.
Notice of Allowance Received for CA Patent Application No. 2,874,853, dated Apr. 30, 2015, 3 pages.
Notice of Allowance received for U.S. Appl. No. 14/404,338, dated May 17, 2016, 7 pages.
Non Final Office Action received for U.S. Appl. No. 14/404,338, dated Jul. 10, 2015, 11 pages.
Alenya et al., 3D modelling of leaves from color and ToF data for robotized plant measuring, May 9, 2011, 7 pages.
Dornbusch et al., ResearchGate: Measuring the diurnal pattern of leaf hyponasty and growth in *Arabidopsis*—a novel phenotyping approach using laser scanning, Functional Plant Biology, Aug. 2012, pp. 860-869, vol. 39, CSIRO, http://www.researchgate.net/publication/259485269.
Havaux, Non-photochemical energy dissipation in photosystem II: theoretical modelling of the "energy-dependent quenching" of chlorophyll fluorescence emission from intact plant leaves, Journal of Photochem. Photobio. B:1993, pp. 97-104, vol. 19, Elsevier Sequoia.
Lenk et al., Special Issue Paper: Multispectral fluorescence and reflectance imaging at the leaf level and its possible applications, Journal of Experimental Botany, 2007, pp. 807-814, vol. 58, No. 4, Oxford University Press.
Moon et al., Fluorescence Imaging System: Application for the Assessment of Vegetation Stresses, Jan. 17, 1997, 10 pages, vol. 2959.
Reuzeau, Traitmille™: A Functional Genomics Platform for the Phenotypic Analysis of Cereals, 2006, pp. 20-24, vol. 4, No. 1.
Rosema et al., Laser Pulse Energy Requirements for Remote Sensing of Chlorophyll Fluorescence Introduction, 1997, pp. 101-108, vol. 62, Elsevier Science Inc.
Samoilova et al., Effects of light environment on the induction of chlorophyll fluorescence in leaves: A comparative study of Tradescantia species of different ecotypes, BioSystems, 2011, pp. 41-48, vol. 105, Elsevier Ireland Ltd.
International Preliminary Report on Patentability Received for PCT Application PCT/US2016/030193, dated Nov. 9, 2017.

\* cited by examiner

Phi2

Reflectance

Phi2 x Reflectance

Phi2 x Light

Reflectance x Light

Phi2 x Reflectance x Light

Phi2

Reflectance

Phi2 x Reflectance

Phi2 x Light

Reflectance x Light

Phi2 x Reflectance x Light

METHODS FOR ESTIMATING PHOTOSYNTHETIC CHARACTERISTICS IN PLANT CANOPIES AND SYSTEMS AND APPARATUS RELATED THERETO

This application is a U.S. National Stage Filing under 35 U.S.C. 371 from International Application No. PCT/US2016/030193, filed on Apr. 29, 2016 and published in English as WO 2016/176612 on Nov. 3, 2016, which application claims the benefit under 35 U.S.C. 119(e) of U.S. Provisional Application Ser. No. 61/154,405 filed on Apr. 29, 2015, which applications and publications are hereby incorporated by reference herein in their entireties.

STATEMENT OF GOVERNMENT RIGHTS

This invention was made with government support under DE-AR0000202 awarded by the U.S. Department of Energy. The government has certain rights in the invention.

BACKGROUND

Photosynthesis is a complex plant process that can be potentially dangerous to the plant under many circumstances. For example, energy captured in the form of photons can exceed the rate at which the energy can be used, resulting in reactive oxygen species (ROS) production and cell damage. Many mechanisms have evolved in plants to cope with this challenge, including some that are fast responding, such as photo protection via the qE response, and others that are slower responding, such as the induction of genes encoding proteins that can detoxify ROS.

It is unknown how these different mechanisms are integrated and the degree to which given mechanisms take precedence under specific environmental conditions. For example, the same mechanisms may be activated in the same series when plants at low temperature are subjected to a change in light intensity, as those that occur when plants that are experiencing drought also experience a change in light intensity. Therefore, understanding how real-time, dynamically fluctuating systems affect plant status (e.g., photosynthetic productivity, efficiency, growth, and the like) are useful for improving a plant's response to the environmental conditions or cues (e.g., abiotic, biotic, and the like).

SUMMARY

Systems and methods for photosynthetic transfer rate estimation in complex plant canopies are provided. In one embodiment, a method of characterizing photosynthesis in one or more plants in isolation and in complex canopies is provided, including capturing a plurality of images of the one or more plants with a sensor, and generating a three-dimensional (3D) model comprising the plant parts of the one or more plants from the plurality of images. In one embodiment, the sensor is a camera. In another embodiment, fluorescence of the plant parts of the one or more plants is measured, and a characteristic of photosynthesis of the one or more plants is derived using the measured fluorescence of the plant parts of the one or more plants and the 3D model comprising the plant parts of the one or more plants.

In another embodiment, fluorescence of the plant parts of the one or more plants is measured by storing a camera image of observed fluorescence and/or light of certain wavelengths that is reflected by the plant parts of the one or more plants is estimated by observing red and/or infrared reflectance of the plant leaves. The characteristic of photosynthesis of the one or more plants is derived using the measured fluorescence of the plant parts, the light absorbed by the plant parts, and the three-dimensional model comprising the plant parts of the one or more plants.

In another embodiment, the three-dimensional model further comprises one or more geometric parameters, comprising at least one of light position relative to the one or more plants, sensor position relative to the one or more plants, and light position relative to sensor position. In one embodiment, position of the sensor relative to the one or more plants is determined by time-of-flight imaging (to indicate depth).

In another embodiment, the depth information is obtained by comparing the fluorescence images with infrared reflectance images.

In a further embodiment, two or more images of the plant taken from different, known locations can be analyzed to obtain depth information.

In various embodiments, images are analyzed to provide estimates of the light absorbed by the leaves at different levels of the canopy, together with estimates of their quantum efficiencies of photosynthesis, which together can be used to estimate photosynthetic processes.

In a further embodiment, the total photosynthesis can be estimated from the images by considering a statistical model of the distribution of leaves at different canopy levels wherein the leaves higher in the canopy can shade leaves lower in the canopy effectively changing the light intensity and also wherein leaves or parts of leaves are obscured from view be leaves higher in the canopy.

Various embodiments described herein provide for more effective characterization of photosynthetic efficiency of plants, enabling researchers to distinguish and cultivate phenotypes having characteristics which improve plant growth, such as improving crop yield. Related apparatus and systems are also disclosed.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 4A'-4F' are schematic representations of the images in FIGS. 4A-4F according to an embodiment.

FIGS. 5A'-5D' are schematic representations of the images in FIGS. 5A-5D according to an embodiment.

FIGS. 8A'-8C' are schematic representations of the images of FIGS. 8A-8C, respectively, according to an embodiment.

DETAILED DESCRIPTION

Figure 1A:
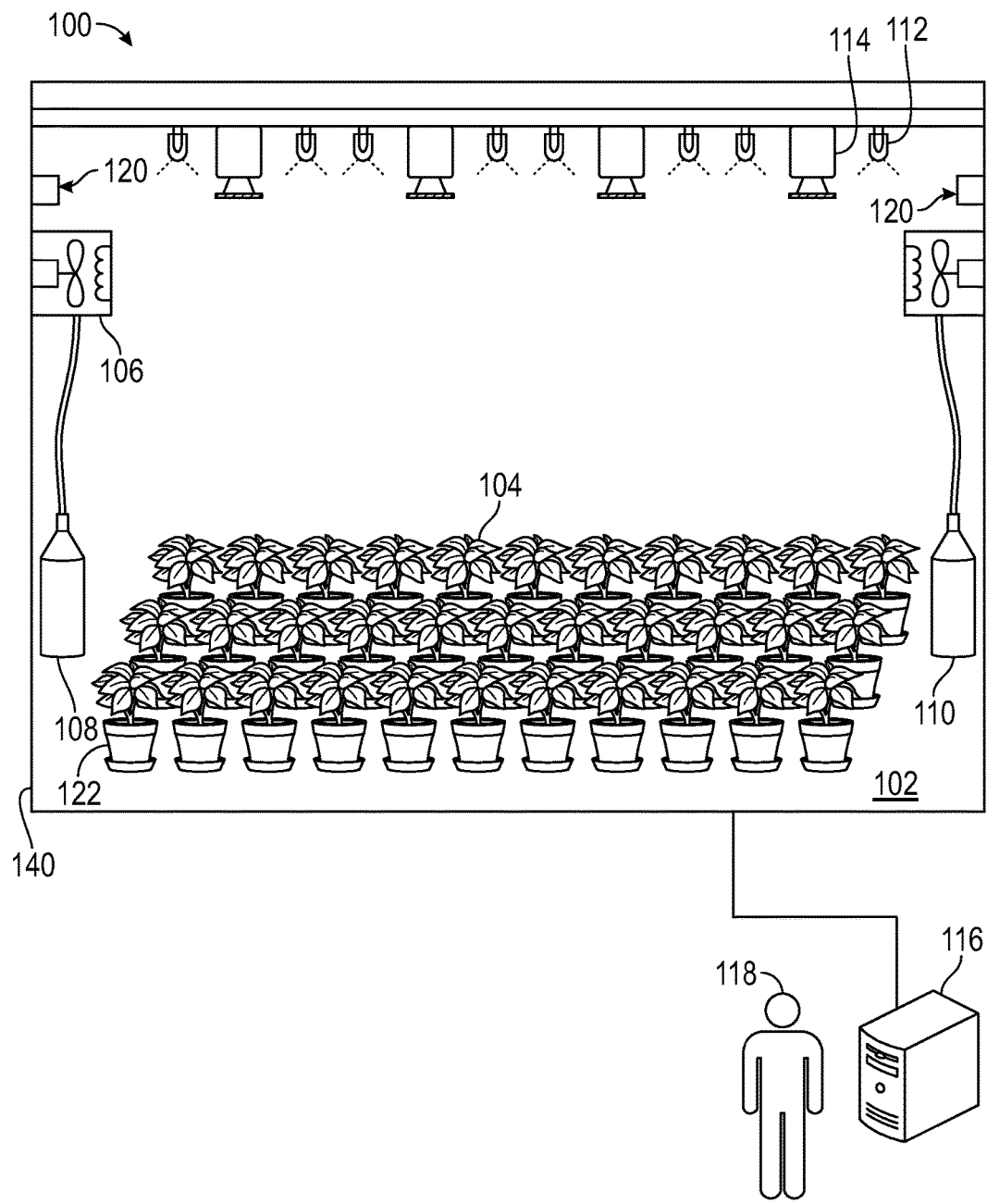
FIG. 1A shows a three-dimensional (3D) photosynthesis modeling system according to an embodiment.

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized, and structural, logical, mechanical, electrical, and other changes may be made. Features or limitations of various embodiments described herein do not limit other embodiments, and any reference to the elements, operation, and application of the embodiments serve only to define these illustrative embodiments.

Features or elements shown in various embodiments described herein can be combined in ways other than shown and described in the various embodiments, and any such combinations is explicitly contemplated to be within the scope of the embodiments presented here. The following detailed description does not, therefore, limit the scope of what is claimed.

Various terms are defined herein. The definitions provided below are inclusive and not limiting, and the terms as used herein have a scope including at least the definitions provided below.

The term "plant" as used herein comprises any multicellular eukaryote of the kingdom Plantae. It includes green plants having cell walls with cellulose that characteristically obtain most of their energy from sunlight via photosynthesis using chloroplasts contain chlorophyll.

The term "photosynthesis" as used herein refers to any mechanism used by plants to convert light energy into chemical energy that can be released to fuel the plant. Photosynthesis includes, in a more detailed example, absorption of energy from light in proteins called reaction centers that contain green chlorophyll pigments.

The term "phototrophic organisms" as used herein refers to an organism that obtains energy from sunlight for the synthesis of organic compounds and include plants, algae and cyanobacteria.

The term "image" as used herein refers to any representation of an object in one or more dimensions, including one-dimensional, two-dimensional, three-dimensional, or greater-dimensional representations of visible, infrared, ultrasonic, or other captured information representing the position of objects being imaged.

The term "sensor" or "imager" as used herein refers to any device, such as a camera or silicon sensory array, configured to capture or record an image or series of images of an object, including in one, two, three or more dimensions. The imagers and sensors can be modified by appropriate selection of sensor filters and light filters to capture light at different wavelengths (colors) to measure different properties of the plants.

The term "camera" as used herein refers to a sensor having a photosensitive surface that records images through a lens.

The term "silicon sensory array" as used herein refers to an imaging device that uses a light-sensitive silicon-based semiconductor array to transfer photonic/image information into electrical information that can be digitized for computer manipulation.

The term "sensor array" as used herein refers to any series of imaging sensors arranged and coordinated in an array to capture images that reflect different properties or at different angles or perspectives.

The term "model" as used herein refers to a representation, whether complete or not, of an object or a process. A three-dimensional model as described herein contains at least some information in three physical dimensions, but need not comprise a complete three-dimensional representation of an object (such as representing only the top surface of a leaf or plant in three dimensions).

The term "plant parts" as used herein refers to one or more organs or regions of a plant such as leaves and flowers having plant cells and able to carry out photosynthesis.

The terms "leaf" and "leaves" as used herein refer to, respectively, one or more organs of a vascular plant that are the principal lateral appendage of the stem. Leaves further include plant cells having chloroplasts that contain chlorophyll, which is used to convert light energy into chemical energy. In some plants such as green algae, algae cells having chloroplasts that contain chlorophyll for purposes of photosynthesis perform this function, and are considered leaves for purposes of this application.

The term "foliage" as used herein refers to the leaves of a plant or plants, collectively.

The term "canopy" as used herein refers to the aboveground portion of a plant or plants formed by the collection of the individual leaves of the plant or plants. In some embodiments, the canopy can include all of the leaves of the plant or plants. In some embodiments, e.g., trees, the canopy may include an upper portion of the foliage of the plant or plants.

The term "light" as used herein refers to electromagnetic radiation in or near the visible portion of the electromagnetic spectrum from about 300 nm to about 1000 nm, including visible light, ultraviolet light, and near infrared light. The terms "light" and "lights" further comprise respectively one or more devices or apparatus configured to emit light, such as visible, infrared, or ultraviolet light.

The term "ultraviolet light" as used herein refers to electromagnetic radiation having a wavelength shorter than but near the visible portion of the electromagnetic spectrum.

The term "infrared light" as used herein refers to electromagnetic radiation having a wavelength longer than but near the visible portion of the electromagnetic spectrum.

The term "actinic light" as used herein refers to light that will stimulate photosynthesis in light-sensitive plants.

The term "light intensity" as used herein refers to the amount of light power over a given area.

The term "Photosynthetically Active Radiation" (PAR) as used herein refers to the light intensity that is effective at activating photosynthesis, typically from about 400 to about 700 nm. PAR is expressed in units or $\mu$moles photons $m^{-2}s^{-1}$.

The term "Phi-2" as used herein refers to the quantum yield of photochemistry (or LEF) at photosystem II.

The term "light quality" as used herein refers to the spectral composition of light that is effective in producing photosynthesis and the support of plant functions.

The term "fluorescence" as used herein refers to the emission of light from material that has absorbed light or other radiation. It specifically includes absorption of sunlight or other actinic or measuring probe light by plants, and emission of energy from the absorbed light as light.

The term "instrument" as used herein refers to any device operable to measure or record a measurable physical characteristic, such as light, temperature, time, or other characteristic.

The term "mapping" as used herein refers to application of one set of information to associated elements of another set of information, such as mapping observed plant reflectance to a three-dimensional model of a leaf or leaves.

The term "multiplying images" as used herein refers to multiplying the intensity values stored in each pixel of one image by the corresponding pixel intensity value of another image.

The term "time of flight" as used herein refers to the time required for incident light to reach the plant part or leaf. It could also relate the time required for emitted light to reach the sensor (e.g., camera) from the plant part or leaf. The "time of flight" for light is approximately equal to the speed of light multiplied by twice the distance from the light source to the camera or detector.

The term "linear electron flow" (LEF) as used herein refers to an electron flow path in photosynthesis resulting from light striking a light harvesting complex in a plant, resulting in the production of ATP, NADPH, and oxygen.

It is known that rapid fluctuations in certain environmental conditions can trigger action of certain protective mechanisms that are not required when the environmental condition is held constant. Plants and other organisms have evolved to cope with unpredictable, dynamically fluctuating environments or conditions, yet study or evaluation of these organisms is conducted largely under constant (laboratory) conditions. While such steady-state observations are very valuable, they are unlikely to detect novel biochemical and regulatory mechanisms that have valuable roles in nature. For example, disrupting key photosynthetic responses often have little effect on growth or photosynthesis in the laboratory, but are strongly deleterious in the field.

Understanding photosynthetic activity in plants enables crop productivity to be increased, such as by increasing photosynthesis under environmental stresses or other changing conditions. Some estimates suggest that up to 70% of plant productivity is lost due to environmental conditions that impact photosynthesis, and understanding how photosynthetic networks respond to changes in environmental conditions has the potential to lead to design of plants with increased photosynthetic efficiency.

To increase understanding of photosynthetic activity in plants under environmental stresses, efforts have been made to determine mechanisms of photosynthetic acclimation to environmental factors. However, these efforts are based on growing plants in highly controlled growth chambers under a given condition, or exposing plants to a change in a single condition, and then following the effects over time on the photosynthetic parameter under study. While this experimental design is useful, such a strategy is unlikely to detect the specific biochemical and regulatory mechanisms that are relevant in nature, such as disruptions in key photosynthetic responses. Such mechanisms typically have little effect on growth or photosynthesis in the lab, but can be strongly deleterious in the field.

Plants can accommodate a wide range of conditions provided they are constant or occur with regularity so that acclimation processes can adjust gene expression, biochemical activities, growth and morphology, etc. Severe stress occurs when the extent of environmental conditions exceeds the physical limits of the organism or when fluctuations occur more rapidly than acclimation responses. Photosynthesis is particularly sensitive to fluctuating environmental conditions. The environmental conditions most directly relevant to photosynthesis, such as light intensity, light quality, temperature, $CO_2$ levels, etc., are the most dynamic in nature (i.e., they change rapidly and over a wide range). If not well regulated, photosynthesis can generate toxic side reactions, especially under fluctuating environments. To prevent this photodamage, the light reactions of photosynthesis are highly regulated. Plants respond to rapid (seconds to minutes) changes in environmental conditions by activating a series of biochemical processes that control light capture, including non-photochemical quenching via the qE mechanism, antenna state transitions, regulation of the thylakoid proton motive force (pmf) via the activity of the chloroplast ATP synthase and ion gradients, and regulation of electron transfer at the cytochrome b6f complex.

Fluctuating conditions can be markedly more harmful than static or slowly appearing conditions for several reasons. Slow onset of conditions can be dealt with using the entire suite of plant regulatory responses. In contrast, rapidly appearing conditions must be dealt with using existing biochemical/biophysical regulatory processes. Individual plant regulatory responses are regulated by different phenomena and respond with different dynamics so that while gradually imposed stress may be compensated, rapid fluctuations may not.

Many genes have clear functions, as demonstrated by losses of function when they are mutated or suppressed. However, lack of knowledge of plant performance under more diverse conditions means that the functions of many genes are obscure; modifying their expression results in little of no apparent phenotypes under laboratory conditions.

Photosynthesis can be modeled and observed using chlorophyll fluorescence imaging to obtain estimates of photosynthetic efficiency, but effectiveness of such methods often relies upon the plants being studied having a relatively simple plant structure that can be easily imaged for fluorescence. It is difficult to apply such methods to many important crop or biofuel plants having complex plant structures consisting of multiple leaf layers, making study and characterization of developmental differences and photosynthetic capacities difficult. In addition, plants grow in complex canopies, e.g., differential heights and overlap of leaves within the canopies, which preclude the estimation of photosynthesis using simple imaging approaches. Additionally, the biochemical and physiological properties of leaves at different levels of the canopies can be distinct, preventing the application of modeling that does not directly measure or consider these differences.

Essentially, complex canopies are highly dynamic and change their structure over a range of time scales, from wind-induced movement on the order of seconds, to changes in light penetration with the position of the sun on the order of hours, to alterations in plant structure and morphology, as well as changes caused by exposure to precipitation. Methods that rely on simple 3D modeling approaches such as modeling by using stereoscope images may not be applicable and/or accurate for complex canopies with leaves that are moved by wind and/or precipitation or which have other plant-induced movements. Other 3D imaging methods which require lengthy image acquisition may also not be feasible in complex canopies.

With respect to specific types of imaging, it is known that linear electron flow (LEF), which is proportional to Phi-2 multiplied by the incident (absorbed) PAR, can be determined by multiplying the Phi-2 image by a scalar PAR value measured at some location near the plant canopy. However, this scalar PAR value may not be representative of the highly variable PAR values localized to specific areas of a plant canopy. LEF images can be conventionally represented by multiplying the Phi-2 image by a scalar PAR value and an assumed absorbance. However, this method can be inaccurate, as it does not follow the variation in light intensity throughout the plant canopy.

Because controlled environment chambers and greenhouses do not reproduce key environmental conditions important for plant responses, research conducted in these devices can miss key biochemical and genetic targets for crop improvement and can also provide misleading indications of potential field performance. Various embodiments described herein remedy this deficiency by better capturing the effects of key environmental dynamics on plant performance using new approaches to phenometric study.

What is needed, therefore, is an approach that characterizes phenotypes under more substantially natural fluctuating environmental conditions in complex plant canopies as are typically found in the field. The systems and methods provided herein allow for measuring of phenotypes under substantially natural environmental conditions by estimating a photosynthetic transfer rate in complex plant canopies, such as by using three-dimensional models of plant canopies. In the various embodiments described herein, a more accurate LEF measurement may be obtained by using localized PAR values determined through imaging. The IR-Reflectance value can be representative of localized light intensity. (See Example). In various embodiments, this improved accuracy can be further refined by including the localized absorbance values for the absorption of red measurement light.

Figure 2A:
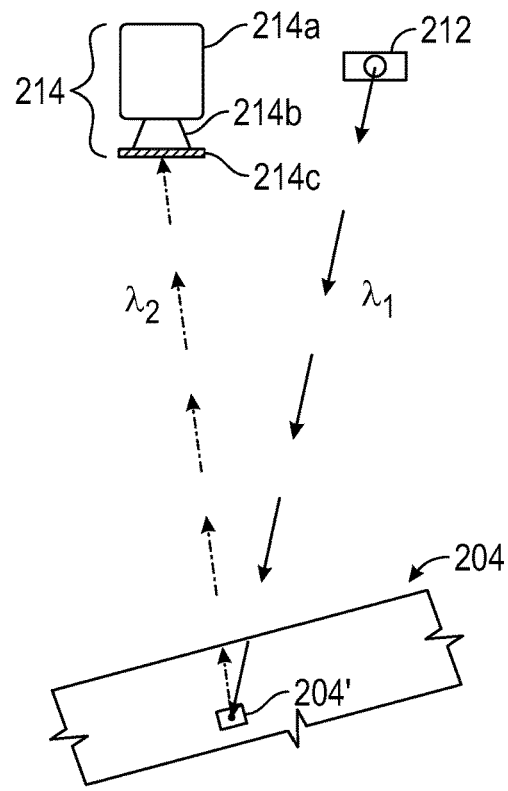
FIGS. 2A-2K are schematic diagrams showing exemplary light sources and camera configurations for obtaining 3D photosynthesis data using a 3D photosynthesis modeling system according to an embodiment.
Figure 2B:
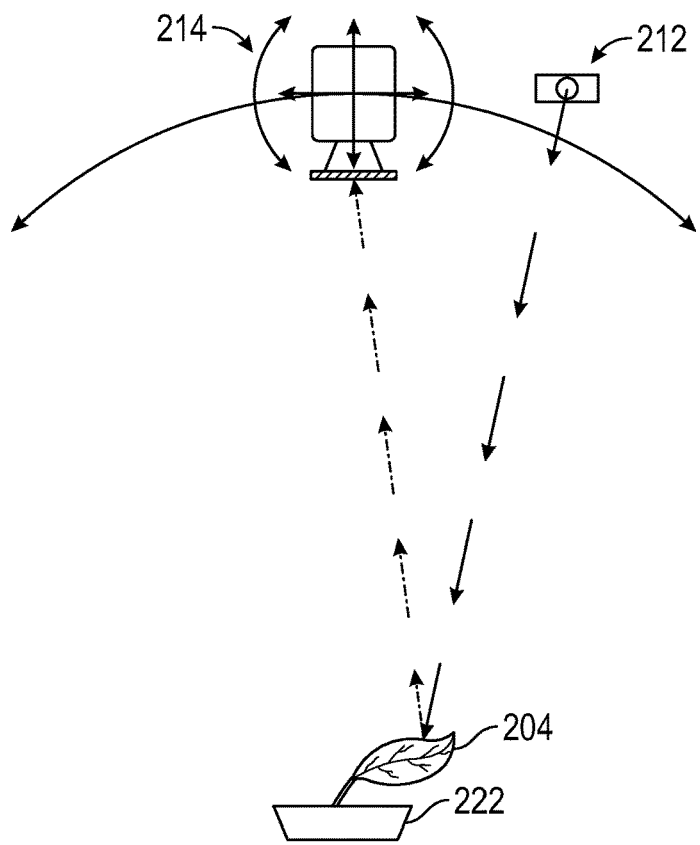
Figures 2C, 2D:
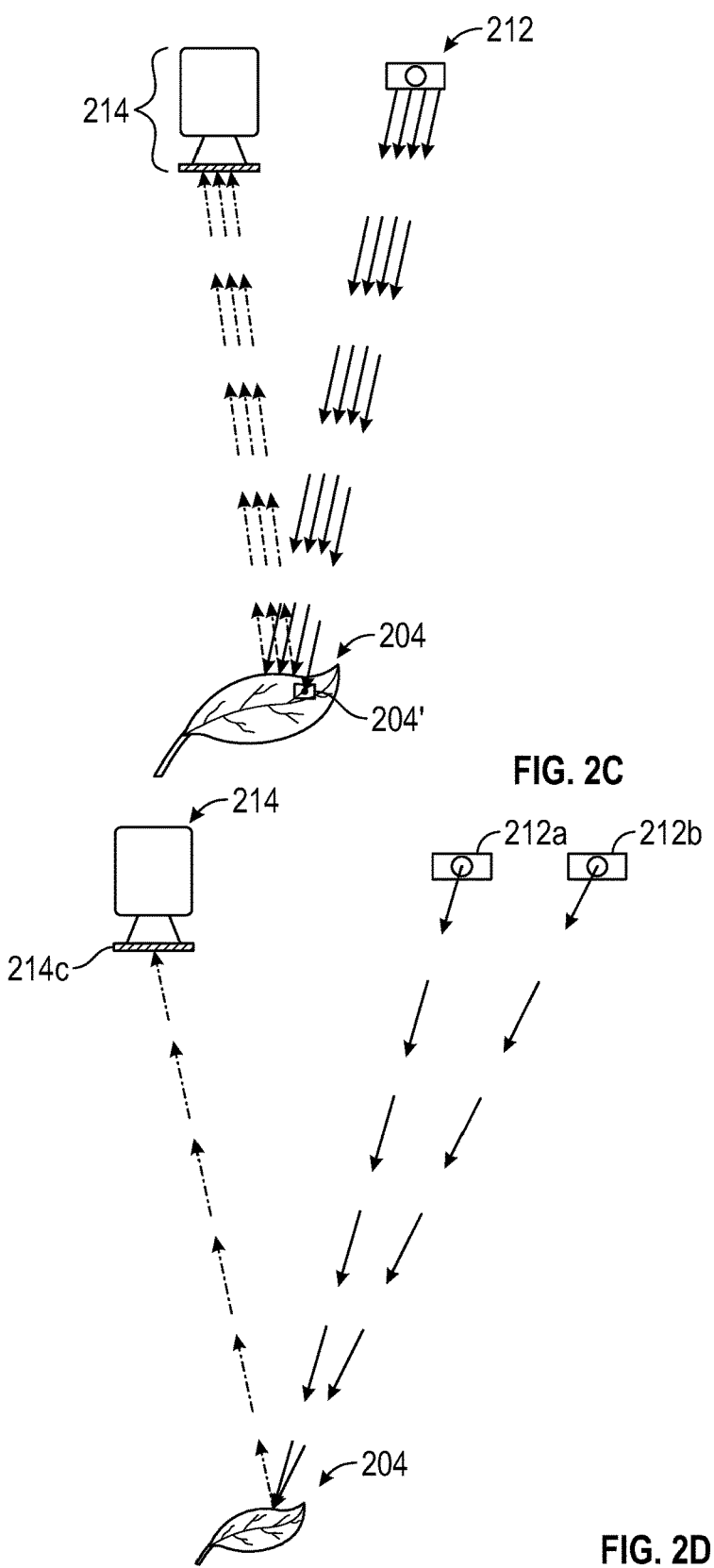
Figure 2E:
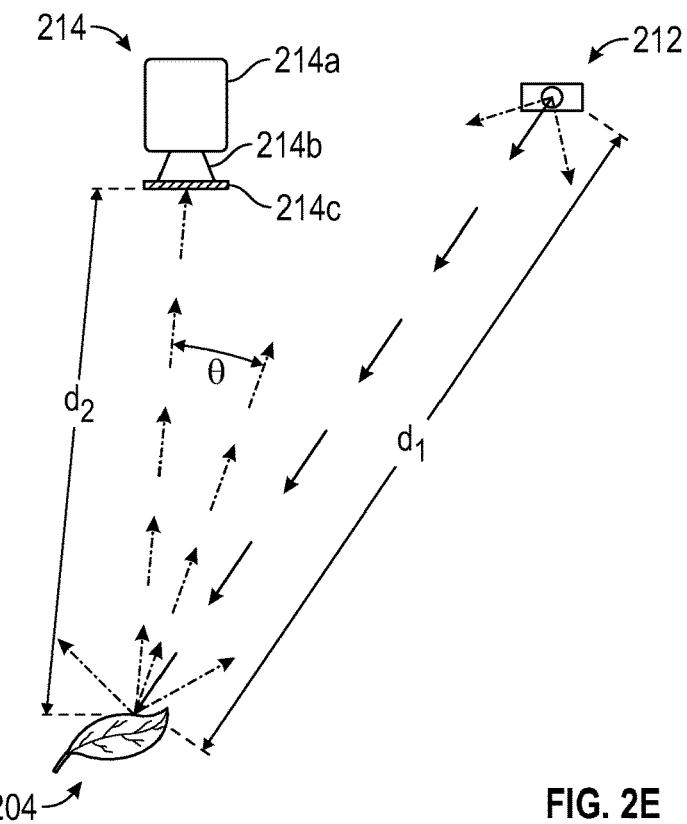
Figure 2F:
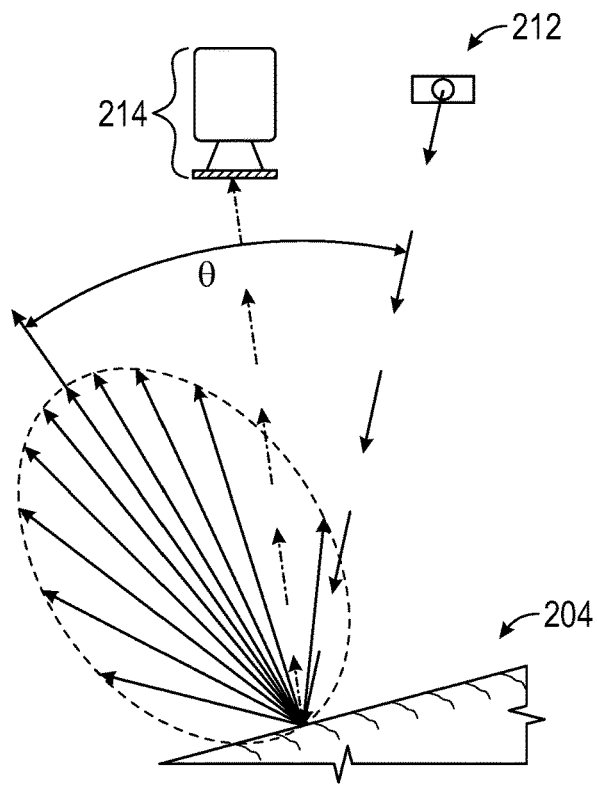
Figure 2G:
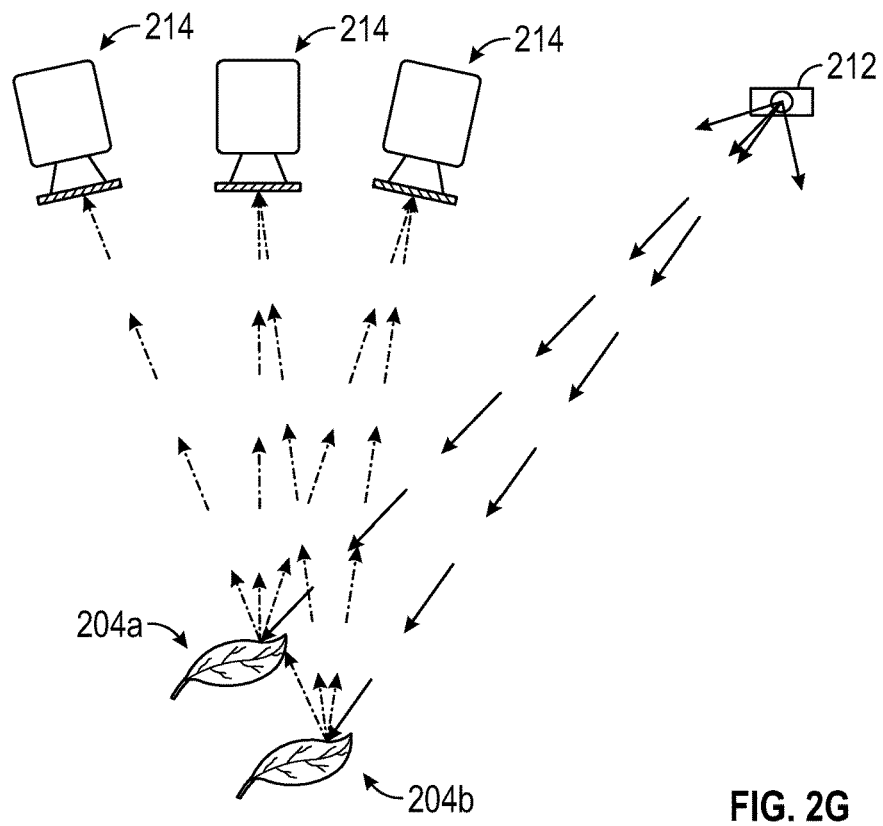
Figure 2H:
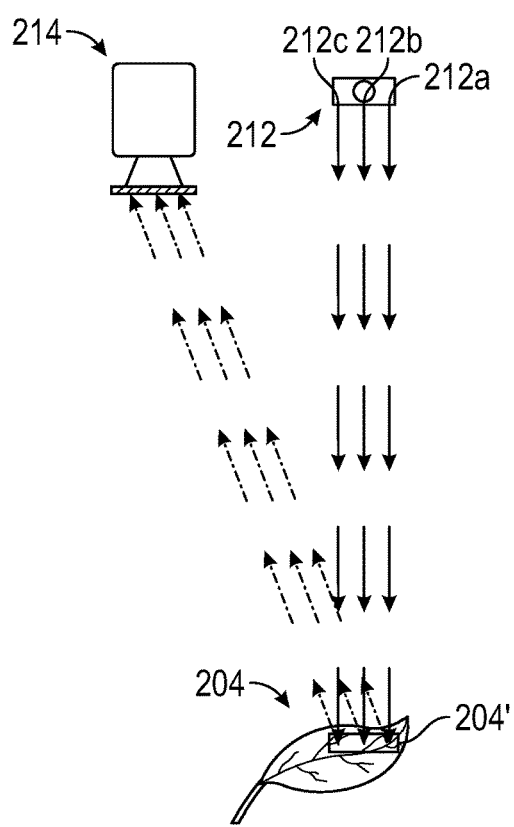
Figure 2I:
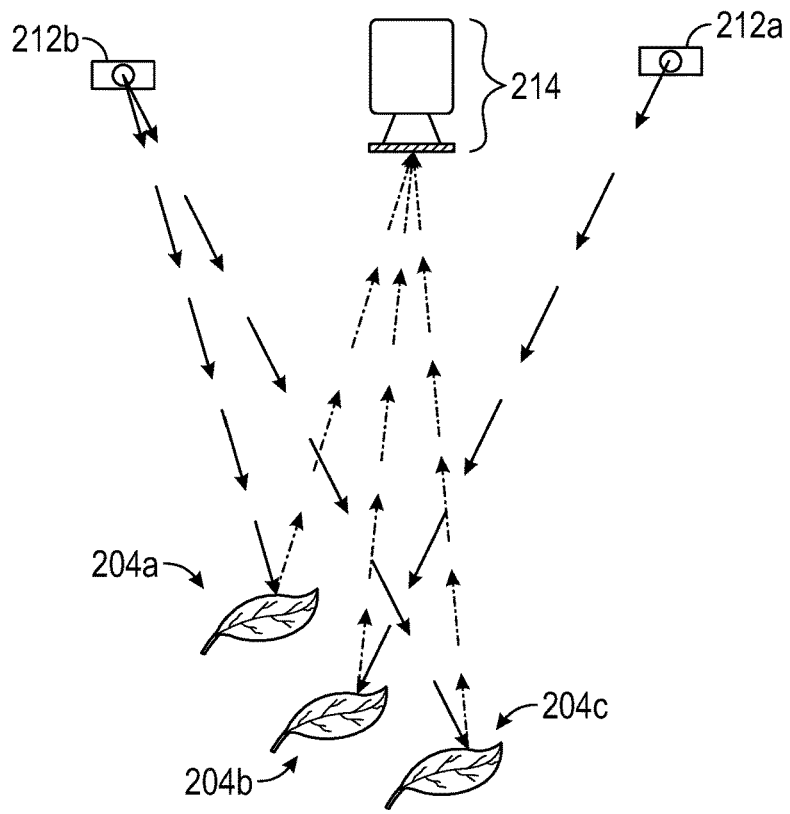
Figure 2J:
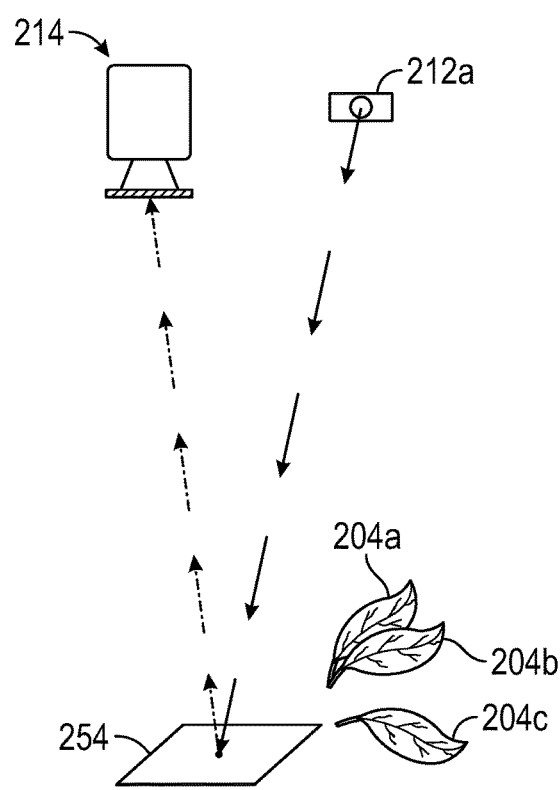
Figure 2K:
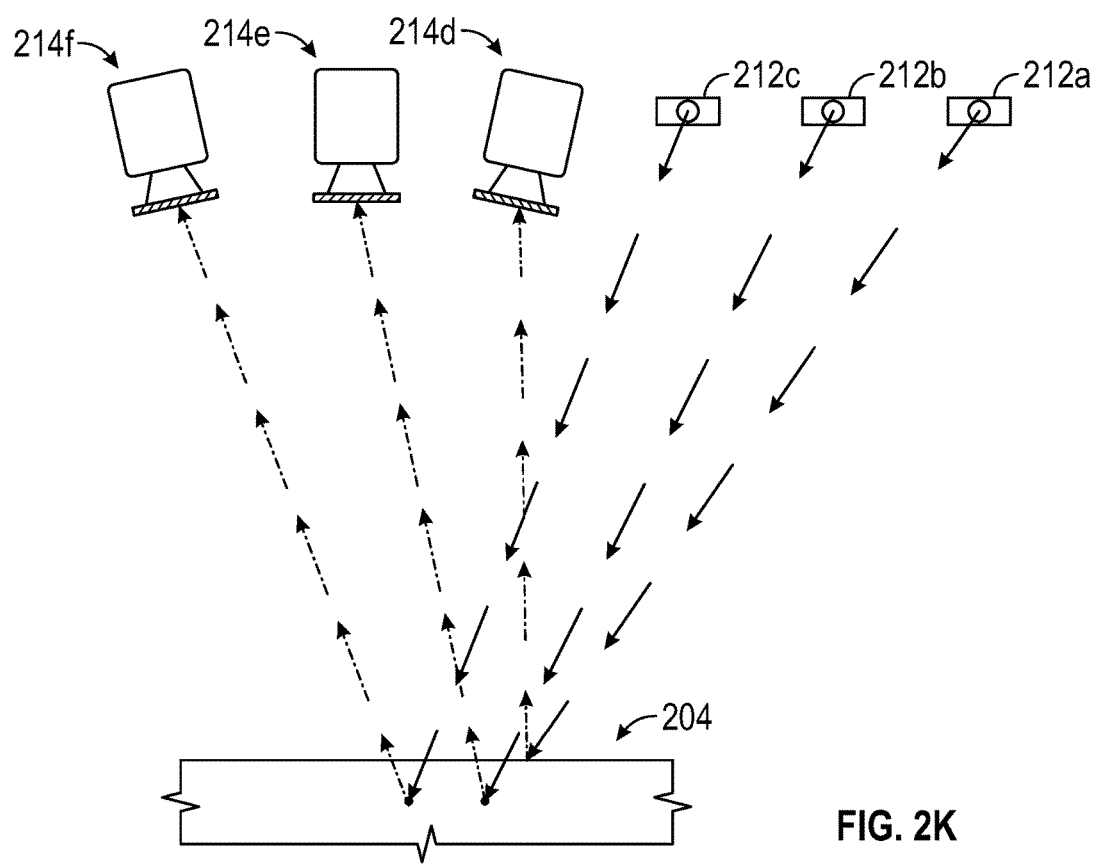
Figure 3:
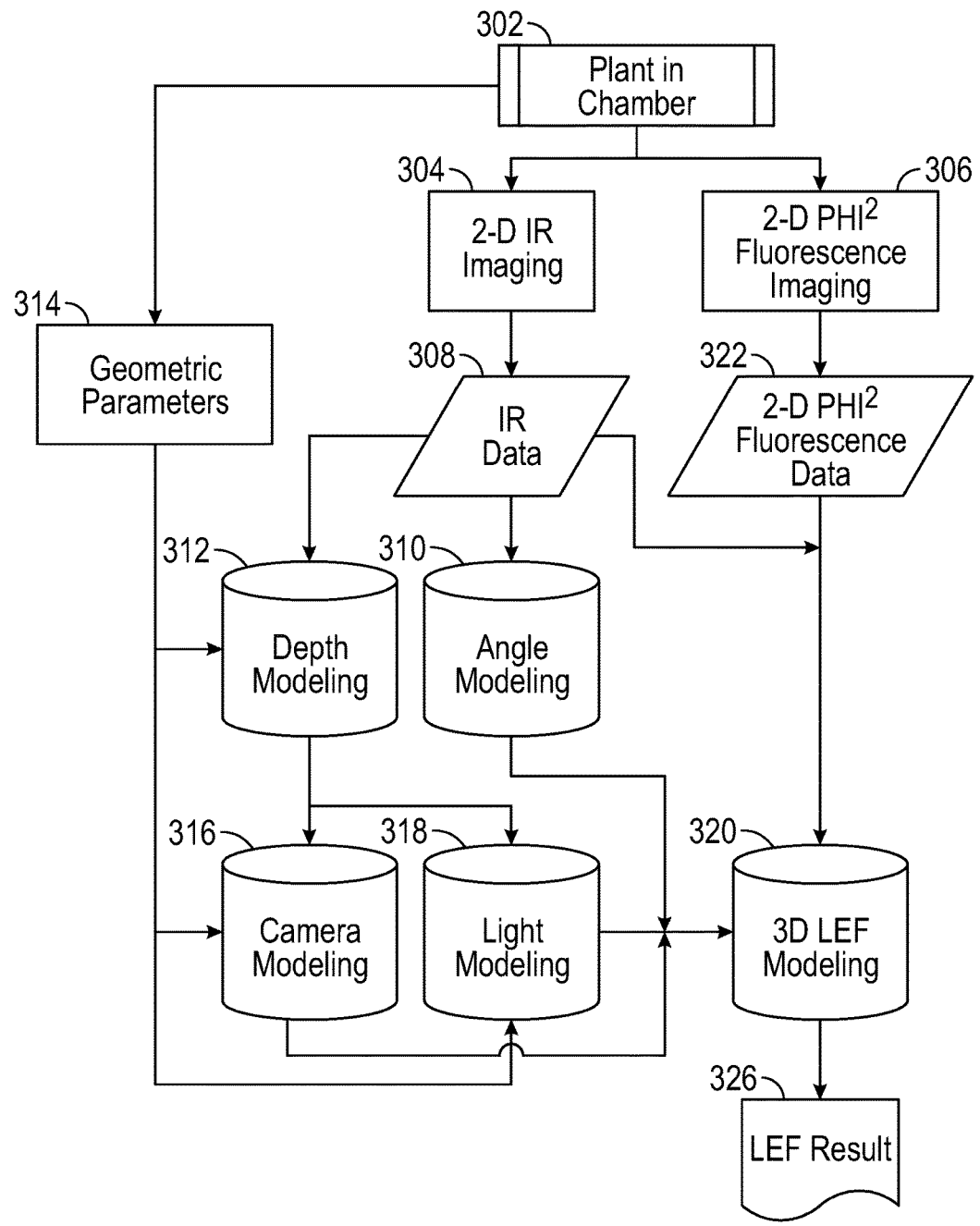
FIG. 3 is a flowchart illustrating a method of estimating efficiency of photosynthesis in a plant canopy according to an embodiment.
Figure 8A:
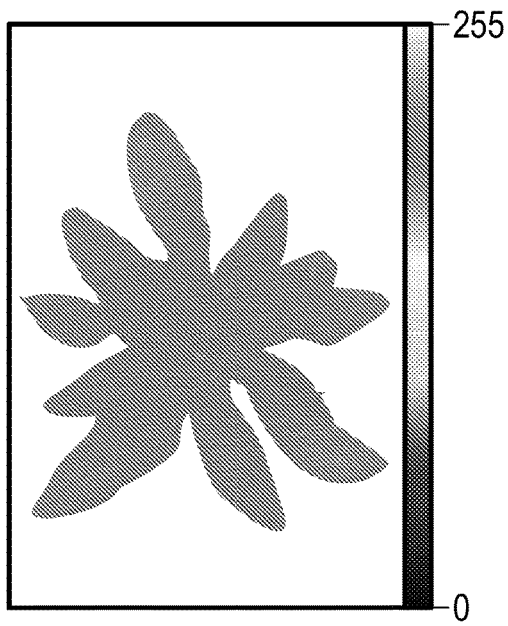
FIGS. 8A-8C are false-color images (with black background removed for simplicity) of a processed relative Phi-2 (LEF) image (FIG. 8A), IR-Reflectance image normalized to peak pixel value (FIG. 8B) and an image of the Phi-2 (LEF) image multiplied by the IR-Reflectance image (FIG. 8C) according to an embodiment.
Figure 8B:
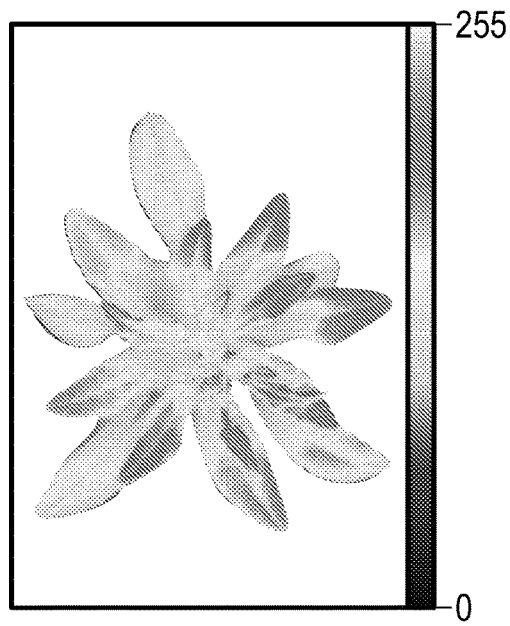
Figure 8C:
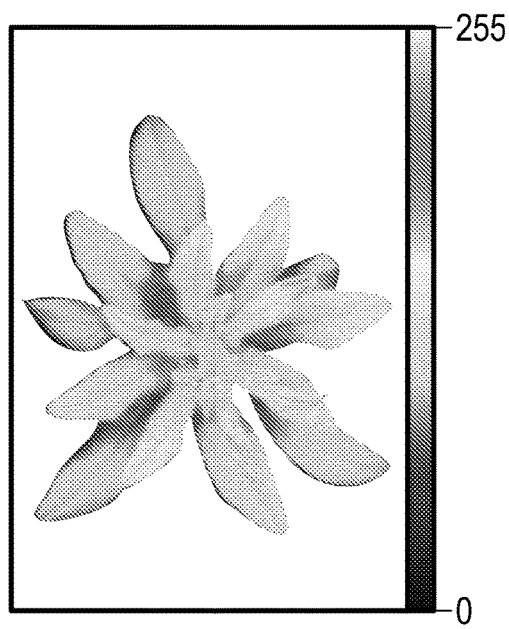
Figure 8A:
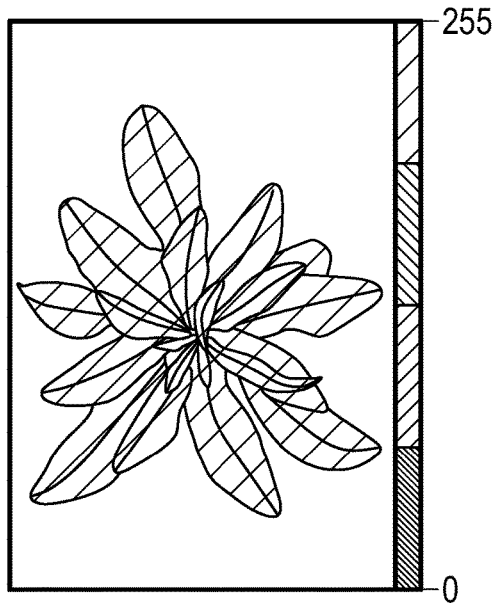
Figure 8B:
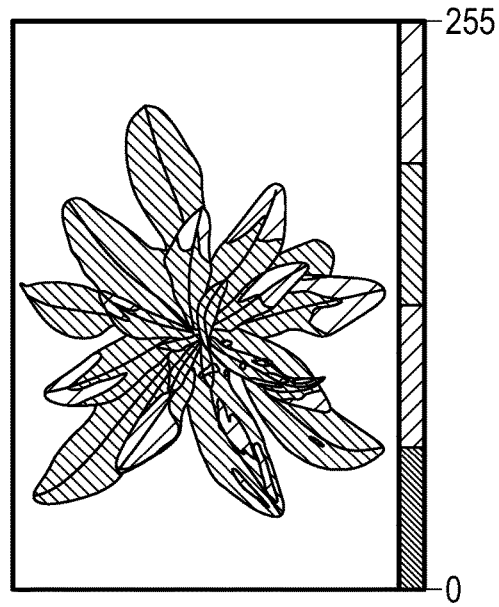
Figure 8C:
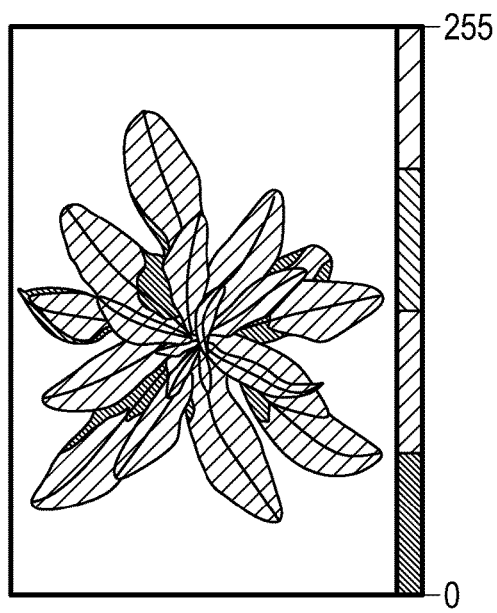

The various embodiments described herein provide for both a 3D photosynthesis modeling method ("3D method") (which combines multiplying and geometric modeling, as shown for example, in FIGS. 3 and 4) and a "multiplying method" which determines information (e.g., photosynthetic characteristics) on plant canopies by multiplying images obtained using lights and cameras at different angles, as described herein, to provide "3D-type" information, as shown in the Example and in FIGS. 8A-8C. This "3D-type" information includes information related to lower plant parts, such as lower leaf layers and/or leaves which may be tilted away from the light, and so on. It is to be understood that the various equipment and apparatus described herein and shown in FIGS. 1A-1G as being useful for the 3D modeling method, and the various configurations of light sources and camera configurations described herein and shown in FIGS. 2A-2K, as being useful for the 3D modeling method, can also be used for the multiplying method.

FIG. 1A shows one embodiment of a 3D photosynthesis modeling system (hereinafter "photosystem") 100 for estimating photosynthetic transfer rate in complex plant canopies. In one embodiment, the photosystem 100 is a three-dimensional (3D) modeling system referred to herein as a "3D-Dynamic Environmental Phenotype Imager (3D-DEPI)" system. In this embodiment, the photosystem 100 includes a chamber 102 in which a plurality of plants 122 can be measured with a variety of associated equipment contained therein. In this embodiment, the plants 122 are arranged side-by-side as they might exist in nature or in a crop plant environment, such that their foliage combines to form a canopy at the top of the plants, although other configurations can be used, including expansion to smaller and much larger scales. Associated equipment includes, but is not limited to, climate control equipment, such as heating and cooling apparatus 106, and humidity control apparatus 120. In a further embodiment, the gas content of the chamber 102 is regulated, such as by controlling the amount of carbon dioxide, oxygen and/or other gasses by regulating, for example, gas tanks 108 and 110 in the chamber 102.

FIGS. 1B through 1G show additional embodiments and/or detailed features of photosystem 100. In the embodiment shown in FIG. 1B, the photosystem 100 includes chamber 102 sized to house the plant or plants 122. The photosystem 100 can include housing 140 configured to accommodate some and/or all of the components of photosystem 100. In the embodiment shown in FIG. 1B, the photosystem 100 further includes tray 134. Plants 122 may be placed on the floor of chamber 102 and/or tray 134. Tray 134 may be removable from chamber 102.

A variety of materials may be used as the housing 140 for photosystem 100. In various embodiments, housing 140 may be polymer based materials, metals such as aluminum, steel and the like. Other materials are also contemplated for the housing and are within the scope of this disclosure. In one embodiment, photosystem 100 may also be a framed structure wherein chamber 102 is not enclosed but is open or partially open on the sides and/or the top. Photosystem 100 can be made from any material that allows isolation of the grow area from the outside environment. In one embodiment, the photosystem can be scaled from about 1 cubic meter to about 3 cubic meters. Photosystems smaller and larger than these volumes are also within the scope of this description.

Figure 1B:
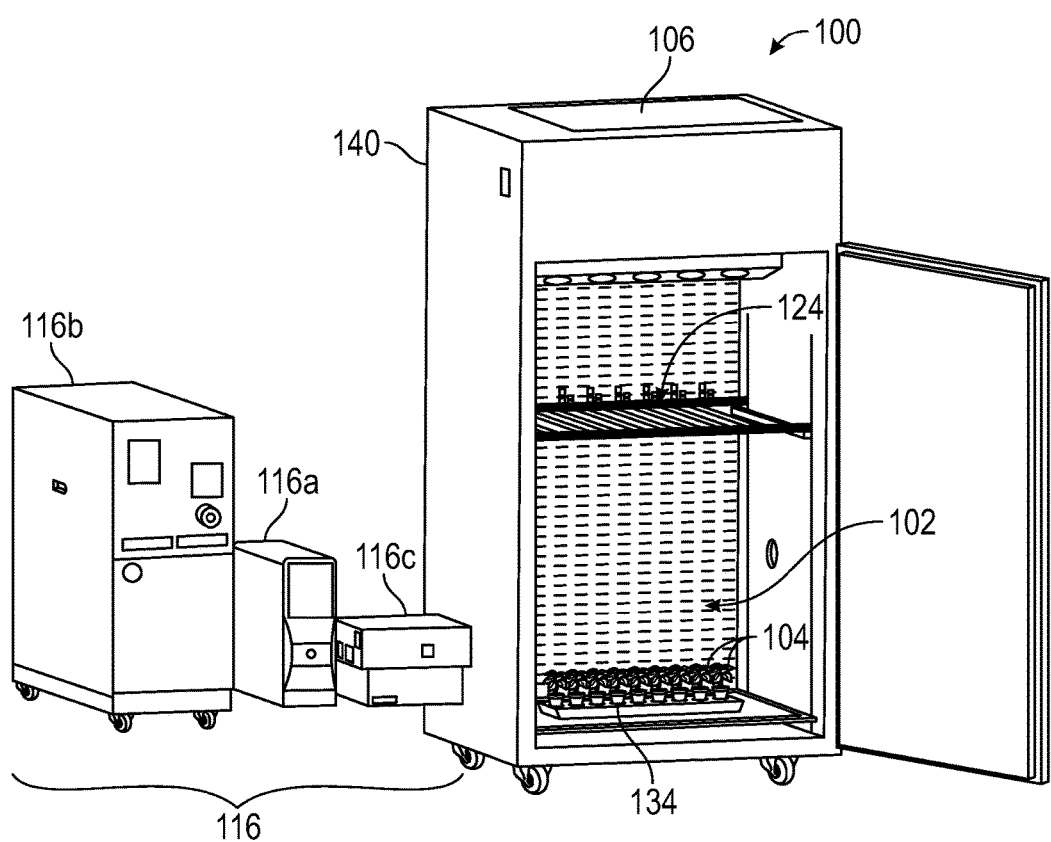
FIG. 1B shows a perspective view of a 3D photosynthesis modeling system according to an embodiment.
Figure 1C:
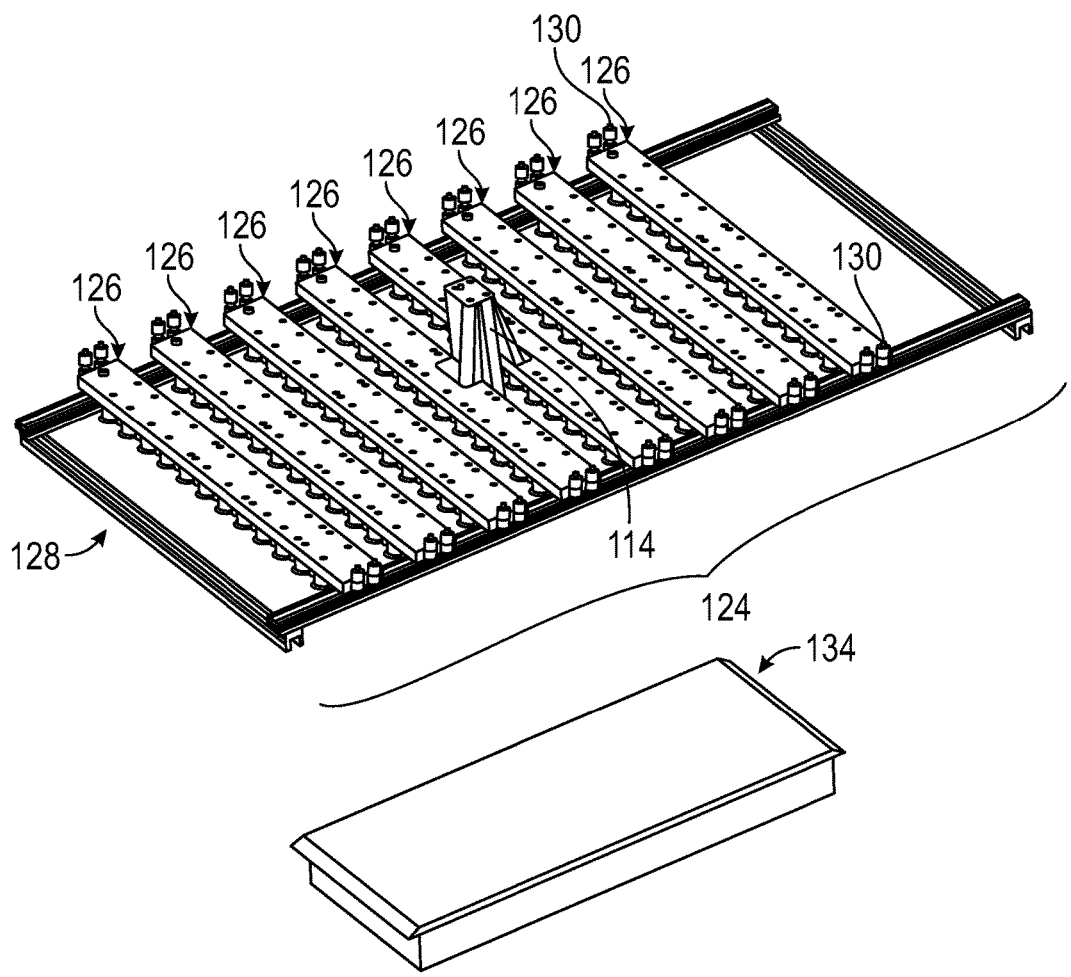
FIG. 1C shows a perspective view of a lighting system and a tray for placing plants in a 3D photosynthesis modeling system according to an embodiment.
Figure 1D:
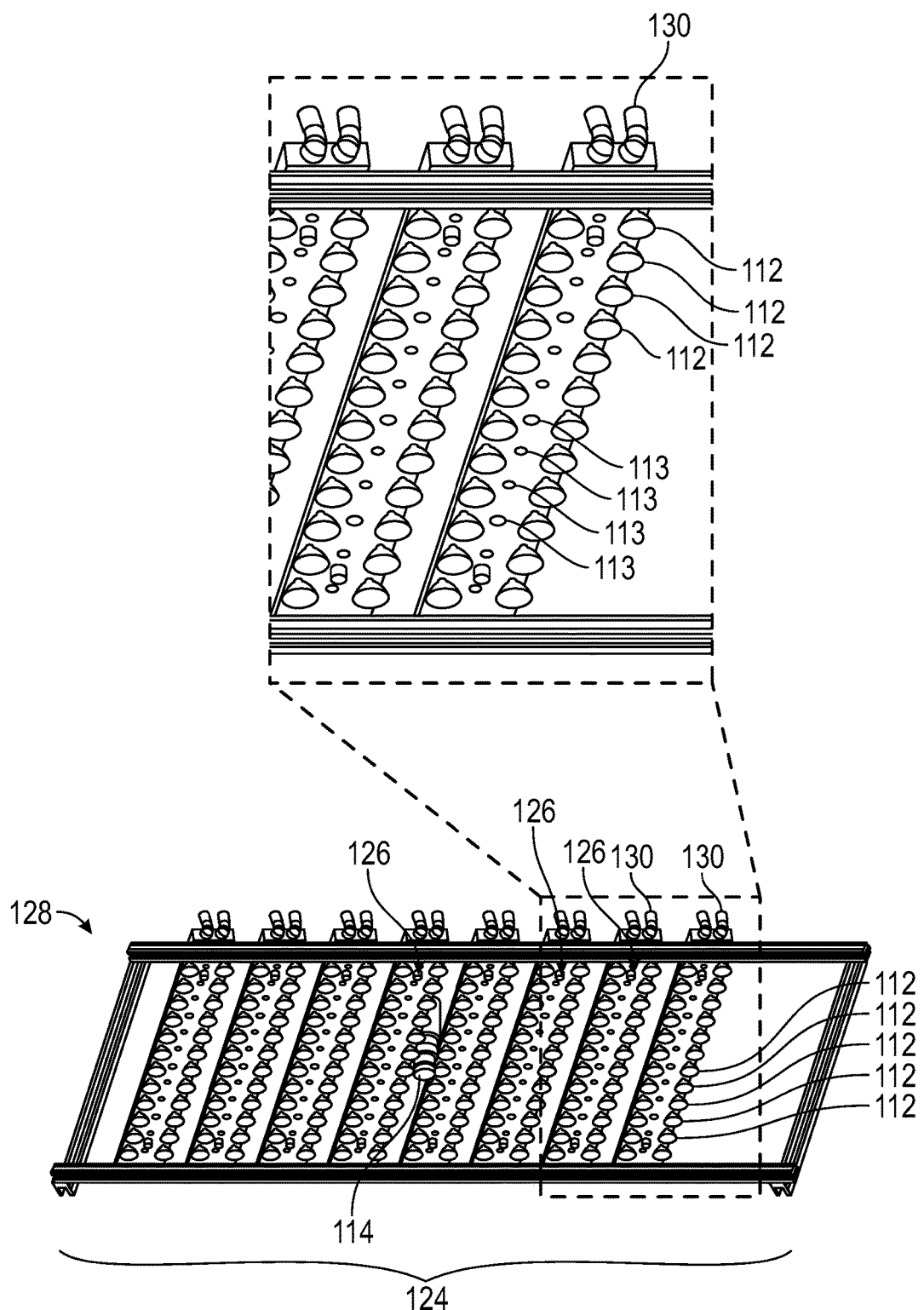
FIG. 1D shows a bottom detailed view of a lighting system in a 3D photosynthesis modeling system according to an embodiment.
Figure 1E:
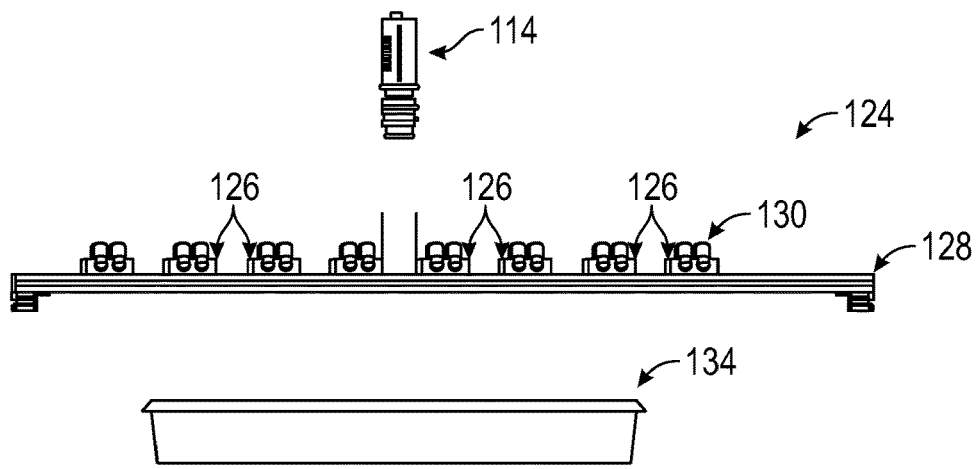
FIG. 1E shows a side view of a lighting system with an unmounted sensor and a plant tray in a 3D photosynthesis modeling system according to an embodiment.
Figure 1F:
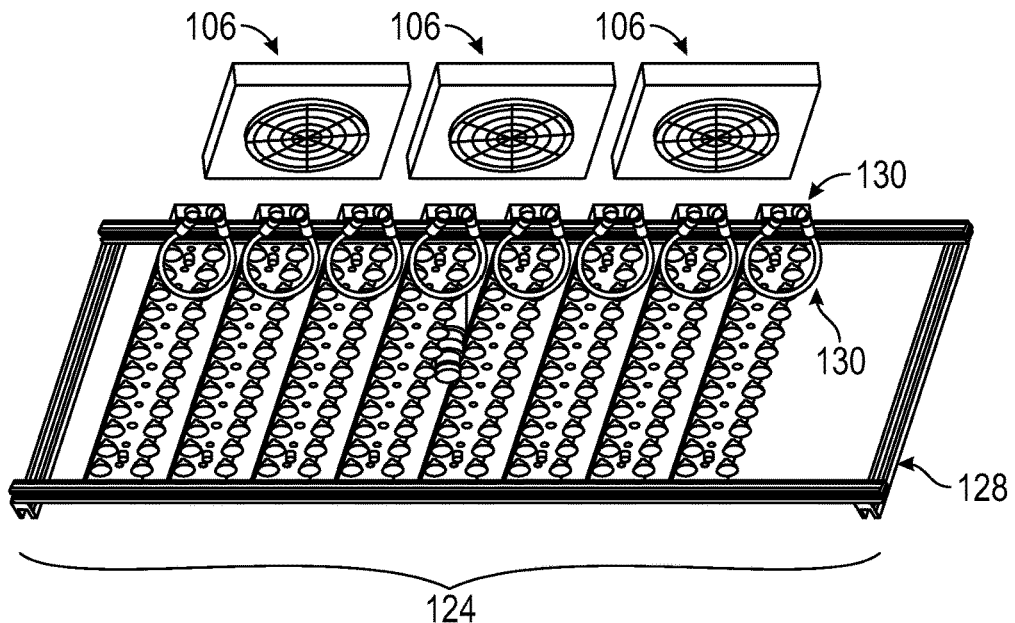
FIG. 1F shows a detailed bottom view of a lighting system and components of a climate control system in a 3D photosynthesis modeling system according to an embodiment.
Figure 1G:
FIG. 1G shows a simplified schematic illustration of a camera in a 3D photosynthesis modeling system according to an embodiment.

As shown in FIGS. 1A-1G, photosystem 100 can further include lighting system 124 comprising one or more lighting arrays 126. As shown in FIG. 1C, in one embodiment, lighting system 124 includes frame 128 configured to accommodate one or more lighting arrays 126. One or more lighting arrays 126 may be mounted onto frame 128. Each of the lighting arrays 126 can include one or more rows of lights with each row including one or more lights 112. In one embodiment, lighting system 124 and lighting arrays 126 are configured as shown in FIGS. 1C-1F. In one embodiment as shown in FIG. 1D, lighting array 126 is shown as having two outer rows of lights 112 and a center row of lights 113, although the various embodiments are not so limited. In one embodiment, center row of lights 113 may be an auxiliary set of lights. Each of the lighting arrays 126 can have the same combination of lights 112 and/or 113, e.g., actinic, infrared, etc. or a different combination of lights 112 and 113. In one embodiment, the auxiliary set of lights 113 may have a lower intensity than the outer row of lights 112. In a further embodiment, the auxiliary lights 113 may have a lower intensity and can be the measurement light source and the outer row of lights 112 can be the actinic light source.

In one embodiment, as shown in FIG. 1D, lighting arrays 126 can include connectors 130 which connect lighting system 124 to heating and/or cooling apparatus 106 by hoses or tubes.

In various embodiments, lighting arrays 126 of lighting system 124 can include lights 112, which can, in one embodiment, include light-emitting diodes (LEDs) such as high color-rendering index LEDs that provide a broad spectrum of light. In the embodiment shown in FIG. 1D, lights 112 can include the actinic lighting source, the infrared lighting source and/or the measurement lighting source. In one embodiment, the high color-rendering index LEDs are from Yuji International. Lighting arrays 126 can also include auxiliary lights 113, which can serve as auxiliary light sources, and, in one embodiment, include an LED array of lights with different wavelength profiles. Lights 112 and 113 may be of same or different sources, emit same or different light intensities and have same or different light qualities to serve different roles in plant illumination or measurement.

Lights 113 can include actinic light sources, infrared light sources and/or measurement light sources. In various embodiments, auxiliary lights 113 can include a plurality of lights, each having a different wavelength profile, such as a red or infrared output, such that the different lights can be selectively controlled to create various light conditions within the chamber 102.

In various embodiments, lights or illumination sources are capable of providing light that simulates sunlight (or the full solar spectrum) and that can be altered. In one embodiment, the light provides actinic illumination. Such actinic light may include light that may activate the photosynthetic apparatus as well as biological light sensors, such as phytochromes, cryptocromes and green light receptors that affect the growth, development and other behaviors (e.g., chloroplast movements) of the organisms.

Light sources may include, in various embodiments, halogen lamps, one or more light emitting diodes (LEDs), lasers, specially designed xenon lamps and the like, and a combinations thereof.

Compared to fluorescent and incandescent lighting, LEDs with appropriate optics can deliver higher light intensities at greater distances with more precise control over light intensity, and more rapid and precise switching (on and off). This level of control allows capturing a fluorescence image generated from a pulsed light of fixed duration and intensity during a brief interval in which actinic illumination is switched off or shuttered.

In one embodiment, the LED illumination system can include a light source that comprises one or more LED or Organic Light-Emitting Diode (OLED), where the LED(s) can emit light at different wavelengths. In one embodiment, white LED lighting may be used as the actinic light. Spectrally, these lights more closely resemble natural lighting conditions that are used for growing plants, as compared to individual or combinations of LEDs of discrete wavelengths. Exemplary white LEDs can provide a wavelength from: about 380 nm to about 750 nm or about 420 nm to about 730 nm, including any range or value therebetween. White LEDs with a colored temperature of from about 5000K to about 7000K, including any range or value therebetween, may also be used. In one embodiment, commercially available white LEDs are used, such as Bridgelux 50 watt white LED arrays or Cree 10 watt white LEDs. In other embodiments, light approximating solar emission can be simulated by combining light from a series of LEDs with a range of emission wavelength that span the solar spectrum. In one embodiment, the overall spectrum may be tuned by changing the emission from each type of LED by adjusting its electrical current.

A measuring light source (e.g., probe or pulsed light) used to excite chlorophyll fluorescence may include white or monochromatic light such as a red, blue or green LEDs or any light within the visible range. Such measuring light may be provided by LEDs (e.g., red LEDs, blue LEDs or green LEDs). In addition, near UV and UV LEDs can be incorporated as supplemental illumination to allow the activating light to better match the solar spectrum and to probe fluorescent pigments in the plant parts or to induce UV-sensitive processes.

In one embodiment, light sources may further include compound parabolic concentrators to collimate the light. Such a configuration may, in some embodiments, better simulate sunlight and allow for higher light intensities to be reached at greater distances. In various embodiments, the light source for growth may be configured or adapted to provide continuous white light intensities at or in excess of full sunlight up to any suitable amount (e.g., fluencies from about 2,500μ moles photons $m^{-2}s^{-1}$ up to about 10-fold (10×) higher than full sunlight, i.e., about 25,000μ moles photons $m^{-2}s^{-1}$), such as about 2×, about 3×, about 4×, about 5×, about 6×, about 7×, about 8×, about 9× higher than full sunlight, further including any range or value therebetween. In various embodiments, photosynthetic measurements may be made at any suitable distance between the light(s) and the plants, such as from: about 0.5 to about 3 meters, about 1 meter to about 2 meters, about 0.5 meters to about 1.5 meters, or at least 1.5 meters, at least 2 meters, at least 2.5 meters, or, at least 3 meters, further including any range or value therebetween. In other embodiments, the distances may be greater or smaller, depending on the size of the plant chamber, the configuration of the camera(s), light(s) and plant(s), and so forth.

In one embodiment, power supplies that support light intensities from about 2400 to about 3000μ moles photons $m^{-2}s^{-1}$, such as in excess of about 2,500μ moles photons $m^{-2}s^{-1}$, up to any suitable amount such as up to 10× higher than full sunlight, including all the ranges and values discussed above, are used, although the embodiments are not so limited. In various embodiments, power to the LEDs may be provided by any suitable source, including DC power supplies, conventional batteries, and the like.

Light intensity and light quality may also be adjusted. In one embodiment, light may be adjusted by regulating the electrical current passing through an LED. This may be accomplished by computer control via an electrical circuit that regulates the conductive status of a transistor or similar device. In one embodiment, a programmable high speed timing card or similar device including a preconfigured Fully Programmable Gate Array (FPGA) or microcontroller can be used to send signals for setting intensity by a control circuit (such as a current limited feedback control circuit) and for rapidly switching actinic light off and on by a rapid gating circuit (such as a rapid switch circuit using MOSFETs and MOSFET controllers).

In one embodiment, light quality can be controlled by supplemental illumination with separate LED arrays of various colors, including ultraviolet, visible and near infrared light. In one embodiment, the light quality (the distribution of light intensity across the solar electromagnetic spectrum near the visible), can be adjusted to match that of solar irradiation or that in different environments. In one embodiment, the light quality may be adjusted to match that measured on a cloudless day, deep within a plant canopy or in commercial greenhouses.

Depending on the environmental condition or the parameter to be evaluated, appropriate sensors may be used. In one embodiment, if light is the environmental cue, various sensors can be used. Exemplary sensors include, but are not limited to, cameras, such as video cameras, high time resolution computer controlled video cameras, cameras with charge coupled devices (CCD), complementary metaloxide semiconductor (CMOS) cameras, and the like. In one embodiment, the sensor comprises one or more cameras. These cameras may be further equipped with optical filters to collect chlorophyll fluorescence images. In one embodiment, the cameras may include filters for far red or near infrared (about 630 nm to about 950 nm) where chlorophyll fluorescence occurs. The sensors can include one or more sensors and may be arranged in any configuration to allow for imaging any area configuration. For simplicity, the term "sensor" is hereinafter used interchangeably with the term "camera," although it is understood that other types of sensors, other than a camera, may be used.

As shown in FIG. 1A, one or more cameras 114 are also provided as part of photosystem 100, which, in various embodiments, are operable to image visible light, infrared or thermal light, ultraviolet light, or other spectra of light. In one embodiment, one or more cameras 114 shown in FIG. 1G include camera body 114a, lens 114b and one or more filters 114c. In various embodiments, one or more cameras 114 have interchangeable filters 114c that enable detection of different light spectra, while in other embodiments the image captured by the cameras can be filtered to image only the wavelengths of interest. In one embodiment, camera 114 is a single camera that is operable to change position within or outside of housing 140. In other embodiments, photosystem 100 comprises a number of cameras 114 used simultaneously as shown in FIG. 1A.

In addition to the aforementioned light(s) 112, camera(s) 114, heating and cooling apparatus 106, humidity control apparatus 120, gas regulating equipment to monitor and regulate gasses in gas tanks 108 and 110, respectively, can be used via a computerized system 116, such as under the command of a user 118. In one embodiment, as shown in FIG. 1B, computerized system 116 can include system 116a for cooling electronics and lighting assembly 124, desktop computer 116b for running program to control the photosystem 100 and to collect and store data, and controller 116c for controlling one or more lights 112 and one or more cameras 114. Other computer components may be used as needed for modulating the components of the photosystem.

In a further embodiment, one or more of the cameras 114 include time-of-flight capability, such as observing or measuring time-of-flight of a laser or other projected signal toward the plant canopy, such that a characterization of distance from the cameras 114 to the leaves 104 of plants 122 forming the plant canopy can be measured and/or imaged.

In various embodiments, the sensor 114 as shown in FIG. 1C may be incorporated into lighting system 124. In one embodiment, integration of multiple cameras into the photosystem 100 allows substantially simultaneous imaging of the entire growing area, thus minimizing data collection time and external stress on plant groups by eliminating the need to move the plants individually from the enclosure to an imaging device.

In one embodiment, photosystem 100 may also be equipped with a sensor 114 wherein the sensor 114 can be used for thermal imaging (e.g., for terahertz (THz) imaging) and spectroscopy. In such embodiments, non-ionizing radiation is provided to the plants 122, or, more specifically, to one or more plant parts, such as leaves, flowers and/or fruits to non-invasively monitor the plant 122. In various embodiments, using THz wavelengths, which are sufficiently short, allow for imaging of e.g., vein and stems. The THz non-ionizing radiation may also be able to be absorbed by water, making it a useful tool to detect plant moisture content in parts of a plant 122, such as in a leaf 104. THz imaging may be used alone or in combination with chlorophyll florescence imaging or other parameters being studied. In such cases, the relationship of water movement and photosynthesis may be evaluated.

In operation, user 118 places one or more plants 122 in chamber 102 and/or on tray 134, and adjusts the environment within the chamber 102 to selected conditions, such as by adjusting lights 112, cameras 114, heating and cooling apparatus 106, humidity apparatus 120, and gas tanks 106 and 108, to provide a suitable mixture of gasses, such as carbon dioxide 108 and oxygen 110, respectively.

In one embodiment, light sources 112 provide various wavelengths or combination of wavelengths. The light source may also, in one embodiment, be configured to allow dynamic control over light intensity, duration and quality. In other words, in one embodiment, the light source reproduces natural light intensity fluctuations that occur under field conditions. To this end, the system may, in various embodiments, be adapted to accept any number of lights, in any suitable combination, allowing the light spectral quality, quantity and duration to be dynamically adjusted. In various embodiments, this capability can assist in simulating the light quality changes that occur at dusk and dawn or the cloud passage, sun flecks in plant canopies or other such situations.

In various embodiments, environmental parameters can be adjusted to allow for the study of photosynthetic properties of the plants 122 under real-world conditions. Such conditions include, for example, partly cloudy days with rapidly changing levels of direct illumination, windy days, humid days, warmer or cooler days, air content and/or combinations of conditions. In one embodiment, the position, number and/or intensity of lights 112 are adjusted. In one embodiment, the position and/or number of cameras 114 are additionally or alternatively adjusted. In one embodiment, temperature is additionally or alternatively adjusted via making adjustments to the heating and cooling apparatus 106. In one embodiment, humidity and air content are additionally or alternatively adjusted. Humidity level can be adjusted by regulating the humidity control apparatus 120 while air content can be adjusted by varying the level of carbon dioxide 108 and/or oxygen 110 gases flowing into the chamber 102.

In plants, visible and near infrared light affect photosynthetic antenna and stomata development that are linked to photosynthetic efficiency. Phytochromes (through far red light perception) are also thought to impact stomatal function during dark-light transitions, but not under constant light. Thus, the ability to alter light quality ratios under fluctuating conditions may result in the isolation of light-dependent components. Given that the plant tradeoff between growth and defense also appears to have overlapping regulation with shade avoidance responses, the ability to alter light quality in the chambers can, in one embodiment, be used for identification and/or examinations of factors related to resource allocation and growth/defense. Further, ultraviolet (UV) irradiation can have strong impacts on plant growth and defense responses, pigment composition and the induction of photo-inhibition of PSII.

Referring again to FIG. 1A, the user 118 is therefore able to control the light provided by lights 112, such as to vary the amount of ultraviolet, visible, and infrared light provided to the plant canopy. In a more detailed embodiment, a first set of lights comprise lights that emit a broad spectrum of visible and ultraviolet light, closely mimicking field conditions across these spectra. One such example is a high color-rendering index (CRI) light-emitting diode (LED) light provided by Yuji International, and a second or auxiliary set of lights providing supplemental infrared. See also the Example Section, where the effect of light variations are studied using plants chosen specifically for their sensitivity to light variation and quality, such as Camelina.

A variety of parameters from a variety of organisms may be studied or evaluated using the disclosed system and method. In one embodiment, any phototrophic organism may be studied.

Plants may include monocots and dicots, including, but not limited to species such as *Arabidopsis*, tobacco, soybean, corn, wheat, rice, cotton and various ecotypes, and the like. The plant species further may be modified by genetic engineering or traditional breeding and also includes plant libraries that have been mutagenized (e.g., T-DNA or chemically). The plants are not limited to any particular development stage and may include early stage plant development. Plants may also be whole plants, plant pans (e.g., stem, leaf), plant preparations (e.g., thylakoid or other chloroplast preparation), tissue cultures (e.g., calli or explants), and cell suspension cultures (e.g., single or lumped).

As noted above, measuring chlorophyll fluorescence provides information on other photosynthetic properties or parameters. Shown below is a table of the parameters that can be measured and the additional information that may be obtained by the disclosed system and method.

TABLE 1

Photosynthetic Characteristics

| Parameters Measures | Measurement | Reflects Measures | Sensor |
| --- | --- | --- | --- |
| $F_v/F_M$ | Photosystem II photochemical efficiency | Efficiency of photosystem II photochemistry | Chlorophyll fluorescence |
| LEF | Linear electron flow, calculated from incident PAR | Rate of photosystem II electron transfer | Chlorophyll fluorescence |
| NPQ | Nonphotochemical quenching | The rate of dissipation of adsorbed light energy as heat reflects the fraction of adsorbed light that is "wasted" as heat. | Chlorophyll fluorescence |
| qE | Rapidly reversible NPQ component | Engagement of photoprotective NPQ responses | Chlorophyll fluorescence |
| qI | Long-lived NPQ | Oxidative photodamage to and repair of photosystem II | Chlorophyll fluorescence |
| qL | Redox status of photosystem II | Backup of electrons in photosystem II resulting from imbalances in light input, downstream sink capacity and photoprotection | Chlorophyll fluorescence |
| PIFR | Postillumination recovery of fluorescence | Activation of cyclic electron transfer via the NDH complex, engaged under environmental stresses | Chlorophyll fluorescence |
| $A_L$ | Leaf/plant surface area | Leaf area, above-ground biomass and growth | Reflectance |
| $dA_l/dt$ | Change in surface area over time | Growth rate | Reflectance |
| $LEF_{total}$ | Total plant LEF, calculated from LEF and AL | Total LEF across the plant | Reflectance and Fluorescence |
| $R_R$ | Relative reflectance and adsorptivity of the leaf | Reflects chlorophyll content and chloroplast orientation | Reflectance |

TABLE 1-continued

Photosynthetic Characteristics

| Parameters Measures | Measurement | Reflects Measures | Sensor |
|---|---|---|---|
| $dR_R/dt$ | Change in red reflectance as a function of time | Light-induced red reflectance changes monitoring chloroplast movements, useful for certain modes of photoprotection | Reflectance |
| $T_L$ and $T_S$ | Leaf and soil temperatures | Transpiration rate, stomatal aperture and dynamics thereof | Thermal imaging |

In one embodiment, one or all photosynthetic parameters may be evaluated as any one of the above parameters may be affected by any set of chosen environmental conditions.

In addition to the light intensity, light duration and spectral wavelength and quality, the temperature, gases, water or nutrient content may be used to evaluate the effect on chlorophyll fluorescence. It should be understood that depending on the parameter to be measured and evaluated, the enclosures with the appropriate environmental cue and sensor may be configured accordingly. Various genes, gene sets and profiles (e.g., regulatory genes and the like) ROS production, metabolites, pigments, seed production, biomass, and the like, may also be evaluated.

Because stomata in plants such as Camelina are finely regulated to balance the needs for efficient absorption of carbon dioxide with the avoidance of water loss and the control of pathogens, the dynamics of stomata regulation are an important field of study for plant growth optimization. It is believed that the dynamics of stomata regulation (i.e., how rapidly stomata respond to changing conditions) are also necessary for this balance, and account for a substantial decrease in photosynthetic efficiency especially under fluctuating environmental conditions. Stomata dynamics are thus a prime target for plant improvement, especially for increasing water use efficiency.

Stomatal dynamics can be monitored non-invasively and in high throughput using thermal imaging (thermography), which reflects evaporative cooling of leaves resulting from transpiration. Referring again to FIG. 1B, the chamber 102 therefore further includes in some embodiments cameras 114 that are operable to observe thermal and/or infrared characteristics of the plant canopy. The combination of photosynthesis and thermal imaging data provided by observing fluorescence and infrared images from the plant canopy can be used to study and characterize plant lines with altered water use efficiency and defense responses.

The photosystem 100 (FIGS. 1A-1F) can be operable to probe important, photosynthetically-relevant, aspects of the plant architecture by imaging the reflectance of light 112 at specific wavelengths of light. Comparing chlorophyll fluorescence imaging with reflectance imaging such as red light and/or infrared light reflectance imaging can provide a more accurate estimate of photosynthesis. The spatially resolved data can also be used, in various embodiments, to indicate regions of the plant in which photosynthesis is limited by light or photosynthetic capacity. The methods are easily applied to large populations of plants 122, either in a chamber 102 (FIGS. 1A-1B) or in field conditions, enabling screening for important photosynthetic properties in many plant lines under diverse environmental conditions. In various embodiments, infrared imaging comprises imaging with infrared, red, or both red and infrared light (e.g., about 635 nm red and from about 735 to about 1100 nm infrared). In one embodiment, chlorophyll fluorescence imaging can include extinguishing actinic light for a brief period, such as up to about 100 milliseconds, and flashing or stimulating the plant canopy with a burst of light such as red light, e.g., measurement light, after which fluorescence can be measured by imaging.

In various embodiments, conditions for capturing images in the photosystem can be manipulated by altering the number of lighting sources, the location of the lighting sources, the type of lighting sources, the quantity and/or the quality of incident light. In addition, conditions for capturing images in the photosystem can also be manipulated by altering the sensors such as the cameras, the number of cameras, the position of the cameras, and the camera filter.

In various embodiments, light sources can be actinic light sources, measurement light sources, and/or infrared light sources. An infrared light source, together with an actinic light source, can be used to estimate the quantity of actinic light absorbed by the plant canopy. Because the two light sources have a known relative light intensity (by means of reflectance standards, known camera response, and/or preliminary measurement) and a similar light distribution and illumination path, an estimate of the total amount of actinic light absorbed by plants can be determined by comparing the amount of actinic light reflected from plants to that of the infra-red light reflected.

Visible light, and especially in the red and blue regions, is strongly absorbed by plant leaves because of the presence of chlorophyll, carotenoids, anthocyanins and other plant pigments. In one embodiment, the actinic light source can generally be the dominant light source driving photosynthesis in the plant canopy, i.e., photosynthetically active radiation or PAR. The intensity measured by an imager of PAR scattering from a leaf surface reflects a number of factors. These factors can include the intensity of the incident light, the extent the leaf pigments absorbed the specific wavelengths range of light used, the distance from the leaf to the imager and the angle of the leaf with respect to the incident light and the camera.

On the other hand, near infrared light is not strongly absorbed by the leaf and is instead strongly scattered in a Lambertian fashion, i.e., back scattering of light from the illuminated surface leaf follows a sinusoidal pattern. The intensity measured by an imager of near infrared (from about 700 nm to about 1000 nm) backscattering from a leaf surface reflects a smaller number of factors, mainly reflecting the incident light intensity, the distance from the leaf to the imager and the angle of the leaf with respect to the incident light and the camera. Images of the backscattered light taken in the visible range with that in the near infrared can be used to estimate the amount of light that is absorbed by the leaf. It can also be possible to use light pulses to measure the efficiency of photosynthesis. In this case, fluorescence from chlorophylls rather than reflectance is probed using a "measuring light" of one wavelength in the region of PAR and measuring the light emitted by the plant parts at wavelengths where chlorophyll emits fluorescence (from about 680 nm to about 800 nm).

The measurement light source can be any light source that can induce chlorophyll fluorescence in a plant canopy. The light from the measurement light source can be partially absorbed by the plant. An amount of the light absorbed by the plant is converted to a different wavelength by means of chlorophyll fluorescence and is emitted from the canopy. The fluorescence emitted from the plant canopy, under various lighting conditions, can be used to determine an estimate of Phi-2 (the quantum yield of photosystem II).

FIGS. 2A-2K are schematic illustrations of various embodiments and details of photosystem 100 showing manipulation of the components such as lighting sources and sensors, such as cameras, in various embodiments to obtain information regarding photosynthetic parameters in a plant canopy. In FIGS. 2A-2K, light sources may be referred to or exemplified as light source 212 but it is understood that the light sources can be lights 212 and/or auxiliary lights 213. The incident light from a light source is indicated by bold arrows. Light emitted or reflected by the leaves of the plant or canopy is shown in dashed arrows directed toward a camera.

In one embodiment, FIG. 2A shows photosystem 100 with light source 212 and an imaging camera 214. In one embodiment, light source 212 of FIG. 2A is an actinic light source that is a broad-spectrum light source. Leaf 204 absorbs some of the light and reflects the remaining light. Camera 214 can be used to acquire images and the specific images captured can be dependent on the selection of filter 214c. Synchronization of light source 212 and camera 214 can also be used to capture images.

In another embodiment, lights 212 of FIG. 2A can be a measurement light source that emits in the region of PAR with a characteristic wavelength or distribution $\lambda_1$, e.g., 630 nm, and is used to illuminate leaf 204 containing fluorescent pigment 204' that can absorb some of the energy from light source 212. An imaging sensor with appropriate sensitivity in the near infrared, but not sensitivity in the PAR region, is used to measure the amount of chlorophyll fluorescence emitted by leaf 204. An amount of the light absorbed by leaf 204 can be converted to a different wavelength or distribution, $\lambda_2$, by means of chlorophyll fluorescence and is emitted from leaf 204 and captured by camera 214 equipped with filter 214c capable of capturing an image of the emitted light of wavelength or distribution $\lambda_2$. In these embodiments, where energy is absorbed by leaf 204, wavelength or distribution of $\lambda_2$ is typically greater (indicating less energy) than the wavelength or distribution of $\lambda_1$ (indicating greater energy).

Camera 214 of FIG. 2A can include an adjustable camera system as illustrated in FIG. 2B. In one embodiment, camera 214 can be raised or lowered relative to leaf 204 enabling the image to be captured at a point closer to leaf 204 or farther away from leaf 204. Moving camera 204 closer to leaf 204 may expose plant 204 to an increase in the intensity or quantity of light that leaf 204. Camera 214, in one embodiment, may also be moved laterally, closer to light source 212 or farther away from light source 212. Lateral movement of camera 214 away from light source 212 can affect the angle and the intensity of the captured image.

Multiple camera angles can be used to gain additional data on the structure of the canopy. Complex plant canopies can result in occlusion so that leaves at the top of the canopy block the view of those at the bottom, preventing measurement of the characteristic of leaves at the bottom of the canopy. By taking images at multiple angles, information regarding under-canopy leaves can be obtained. In one embodiment, images from a range of angles using multiple camera angles can be used to obtain a reasonable representation of the canopy. Increasing the number of images obtained at different angles can increase the accuracy of the representation of the canopy.

In one embodiment, the images captured at different angles can be as close in time as possible to avoid interference from leaf movements.

In one embodiment, multiple cameras can be used to obtain multiple camera angles. Statistical analyses may be performed to combine the data from the multiple cameras to gain a reasonable estimate of the properties of the plant parts. In one embodiment, multiple angles can be obtained by moving the camera and analyses of the images can be performed to combine the data from the images at the different angles.

FIG. 2C shows an embodiment demonstrating that the measurement of reflectance of light by leaf 204 exposed to light from light source 212 can be used to determine the amount of absorbed light. Light source 212 can emit multiple wavelengths of light, e.g., in the PAR and the near IR, with the same trajectory or directionality. In other words, the near IR and the actinic PAR have the same or similar angles with respect to the plant canopy.

In FIG. 2C, light source 212 emits an initial quantity, x, of light directed at leaf 204. Light source 212 can be, in various embodiments, an actinic light source and/or an infrared light source. When leaf 204 is exposed to light from light source 212, a quantity of light, y, is absorbed by leaf 204 via fluorescent pigment 204'. The remaining quantity of light, z, not absorbed by leaf 204 is reflected. Measurement of reflected light, z, by camera 214 can be used determine the quantity of absorbed light, y, since the quantity of reflected light, z, is proportional to the quantity of initial or incident light, x directed at leaf 204.

In various embodiments, varying the angle of the light with respect to the camera can be used to obtain information regarding the under-canopy leaves and obtain information regarding the canopy. In one embodiment, the photosystem 100 can include two different light sources. As shown in FIG. 2D, in one embodiment, the two different light sources can have different light quality and can be, for example, an actinic light source 212a and a measurement light source 212b. In one embodiment, the two light sources 212a and 212b can have the same light quality. Both light sources 212a and 212b can be directed to the same area of leaf 204. One or more images can be captured by camera 214. Different images can be captured by camera 214 by varying the selection of the filter 214c and/or the synchronization of light sources 212a and 212b with camera 214.

FIG. 2E shows the use of light source 212 and camera 214 in an embodiment of photosystem 100 to determine spatial measurements based on time of flight analysis. Light source 212 and camera 214 are as indicated and the resultant path of the incident light and emitted light are as shown. In this embodiment, time of flight data can also be measured to obtain distance, d1, between light source 212 and leaf 204 and distance, d2, between leaf 204 and camera 214. The angle, θ, between leaf 204 and camera 214 is determined by the positioning of the camera with respect to the imaging detector. The camera is the imaging detector and the leaf angle can be determined by analysis of the time of flight information.

In one embodiment, FIG. 2F shows that light intensity measured by camera 214 can be dependent on orientation of leaf 204 relative to light source 212. Incident light from light source 212 results in a vector field of light emitted from leaf 204 based on the orientation of the surface of leaf 204. The effect of the multiple light angles is to illuminate different sub-sections in the understory leaves and other plant parts. With each angle, different understory leaves and parts of the leaves will be shaded or exposed to the illuminating light. Comparing images taken from each angle will reveal the depth of understory plant parts with respect to the top canopy leaves.

FIG. 2G illustrates an embodiment using multiple cameras to image different views of the plant or plant canopy. In FIG. 2G, three cameras 214 are positioned at different locations and incident light path is shown from light source 212. Multiple leaves 204 of the plant or plant canopy are shown. Top leaf 204a, for example, can block some of the incident light and/or emitted light from bottom leaf 204b. Each of cameras 214 can be used to image different views of the plant canopy, wherein the light paths can be shown blocked in some images from cameras 214 but not in others dependent on the location of the camera placement. The effect of the multiple camera angles is to image different sub-sections the understory leaves and other plant parts. With each angle, different understory leaves and parts of the leaves will be exposed to the imaging sensor. Comparing images taken from each angle will reveal the depth of understory plant parts with respect to the top canopy leaves.

In a further embodiment, FIG. 2H shows light source 212a, 212b, and 212c follow the same path to expose the same area 204' on leaf 204. Each of light sources 212a, 212b, and 212c can be different or same types or quality of light. In one embodiment, light source 212a can be an infrared light source, light source 212b can be a measurement light source, and light source 212c can be an actinic light source. In various embodiments, the measurement light source can be any fluorescent excitation light source such as visible light, e.g., red light or ultraviolet light. In this embodiment, the angular dependence of the images can be compared with the reflectance backscatter in the PAR and near infrared regions to provide a refined estimate of the absorbed light throughout the plant canopy. This approach can allow estimation of both the degree of occlusion at different angles as well as the angular dependence of reflectance of the measuring light with respect to the plant parts. In turn, these results can be analyzed using Lambertian behavior of plant leaves to light, to determine the curvature and/or planarity of the leaves as well as the degree of light absorption by PAR relative to the near infrared.

In one embodiment of photosystem 100, FIG. 2I shows that the lighting sources can be placed in two different positions to illuminate different leaves or leaf portions of a canopy. In some lighting positions, leaves may or may not be illuminated. By using multiple lighting positions, multiple images can be captured of the canopy for development of the photosynthesis 3D modeling. As shown in FIG. 2I, leaves 204a, 204b and 204c are exposed to incident light from light source 212a and 212b. Camera 214 can be used to capture images and includes emitted light from multiple leaves. Leaves 204a and 204c can be, for example, exposed to incident light from light source 212b whereas portions of leaf 204b can be exposed to incident light from only light source 212a. The compilation of images obtained from camera 214 provides information regarding leafs 204a, 204b and 204c.

In one embodiment, FIG. 2J shows the use of a reflectance and/or fluorescence standard in a canopy to quantify the amount of light reaching the canopy. By measuring the amount of incident light from light source 212a reaching reflectance standard 254 while knowing the reflectance of the reflectance standard 254, the quantified response for camera 214 can be determined. As such, the light emitted from leaf/canopy 204 to camera 214 is quantified and can be compared to the incident light toward canopy 204. In this embodiment, a standard leaf-shaped object with known geometry and optical properties is placed within the chamber to provide a means of standardizing or normalizing the results. The standard can have reflectance and fluorescent properties that mimic the plant materials and can be placed both in the open (without obstructions) and within the plant canopy, to provide a validation of the measurements.

In one embodiment of photosystem 100, FIG. 2K shows multiple light sources and multiple cameras that can be modulated to provide different understory illumination and camera angles to determine the efficiency of photosynthesis throughout the plant canopy. This can provide a more detailed representation of the plant canopy. Light source 212a, light sources 212b and light source 212c can be, for example, the infrared light source, measurement light source and the actinic light source, respectively, with leaf 204 exposed to all three light sources. Cameras 214d, 214e and 214f can be used, for example, to capture images from light sources 212a, 212b and 212c. In one embodiment, a single camera may also be used to capture images resulting from light sources 212a, 212b and 212c.

The lights, cameras, and other components that simulate varying weather conditions such as humidity, gases, wind, heating and cooling may be manipulated and images captured to provide information related to 3D photosynthetic parameters in a plant or a plant canopy.

FIG. 3 is a flowchart illustrating an example method of estimating efficiency of photosynthesis in a plant canopy. Here, plants are placed in a chamber at 302, such as the chamber 102 of FIG. 1A or in a field that is configured for observation. Two-dimensional infrared images are collected at 304, and two-dimensional Phi-2 fluorescence imaging is collected at 306. The infrared images are used not only for plant characteristic measurements such as light/dark transition measurements, but for determining the size and position of the leaves of plants 122 that make up the plant canopy and contribute to photosynthesis. The infrared data is therefore collected at 308, which in some embodiments comprises multiple images of the same region of the plant canopy from different angles. These multiple images are then used to generate angle modeling of the leaves that make up the plant canopy at 310, as well as to model the depth of the plant canopy at 312, such as where multiple layers of leaves have varying degrees of exposure to illumination from above.

Various geometric parameters of the plant canopy and configuration, as well as the configuration of the cameras (and lighting in some embodiments) as shown at 314 are used along with the depth modeling data generated at 312 to generate a camera model 316 and light model 318. These models of depth and angle of plant foliage, as well as position of lighting and cameras, are then used to generate an approximation of a 3D model at 320.

More specifically, knowing the angle of a plant leaf relative to one or more lights enables calculation or estimation of the amount of light reaching the leaf from each of the lights such as 112. A leaf that is perpendicular to the direction of travel of light will receive a full dose of light across the surface of the leaf, while tilted leaves will receive less light depending on the angle of tilt, calculated such as by multiplying the light intensity by the cosine of the angle between the direction of light travel and the tilt of the leaf. Angles such as these are modeled at 310 in this embodiment, while calculations based on the angle modeling are performed at 320.

Similarly, the distance from each light to each leaf is also employed to determine the amount of light reaching each leaf, based on the distance from the light to the leaf and the brightness of the light. This is reflected by depth modeling at 312 in this example, where a model of the depth from light sources to modeled leaves are determined based on factors such as the geometry of the growth chamber at 314 and the infrared or other measurements at 308. Distance information in a further embodiment is determined using time-of-flight measurements, such as by sending a light such as a laser, or another signal such as an ultrasonic pulse, from a device such as a camera 114 to the plant canopy and observing the time taken to receive a return signal. In other embodiments, interferometry or other signal processing techniques are employed to measure time of flight, or to otherwise measure distance from a known location to one or more leaves in the plant canopy.

Once an accurate model of the lighting and camera configuration are used to generate an accurate model of the leaf configuration, the three-dimensional models are used to model characteristics of the plant canopy at 320, such as photosynthetic efficiency. In a further embodiment, this is based at least in part on observed two-dimensional Phi-2 fluorescence image data obtained at 306 and stored at 322, such as imaging the chlorophyll fluorescence of the leaf canopy very shortly after turning off actinic light provided to the plants being studied, or measuring fluorescence very shortly after turning off a pulsed light or stimulating light provided to the plant canopy soon after (e.g., 200 milliseconds after) extinguishing actinic light. In other embodiments, other methods such as radiometry, color spectrometry, and infrared or thermal imaging are employed to measure one or more plant characteristics such as photosynthetic efficiency or activity.

Here, the three-dimensional linear electron flow (LEF) modeling performed at 320 is based on the observed two-dimensional Phi-2 fluorescence image data 322, which indicates the absorption of light by antennae complexes that funnel the light energy into photosystems within the plants. The plant photosystems oxidize $H_2O$ and reduce $NADP^+$ to NADPH in a process called linear electron flow (LEF), which is modeled to determine the rate or efficiency of photosynthesis in the plants. Because light absorbed by chlorophyll molecules in a plant leaf are either used to drive this photosynthesis process, are dissipated as heat, or are re-emitted as chlorophyll fluorescence, measurement of a plant's chlorophyll fluorescence can be used along with other information such as the amount of light striking the leaf to estimate the efficiency of photosynthesis (and consequently, photosynthesis characteristic elements such as linear electron flow).

In the embodiment of FIG. 3, a complete traditional three-dimensional model need not be created, as the depth and angle information along with a geometric model including camera and light information can be used to estimate the area of each leaf of the canopy and compensate for any effects due to varying angles or positions of the leaves, cameras, and lighting. This enables accurate modeling of the plants 122 without creating a complete traditional three-dimensional model of the plant canopy and surrounding environment, typically employing complex math such as ray tracing and shading that are very computationally intensive. The method of estimating photosynthetic efficiency of FIG. 3 does not require such computationally complex steps, and so is more readily employed using relatively inexpensive systems such as a personal computer as the computerized system 116 performing the functions recited in FIG. 3.

Figure 4A:
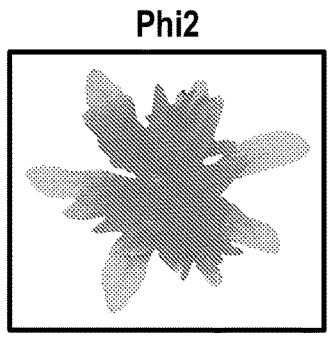
FIGS. 4A-4F are false-color images (with black background removed for simplicity) showing Phi2 of a plant (4A), IR-reflectance of the plant (4B), Phi2×reflectance (4C); Phi2×light (4D), reflectance×light (4E) and Phi2× reflectance×light (4F) according to an embodiment.
Figure 4B:
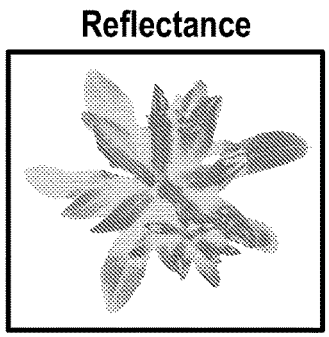
Figure 4C:
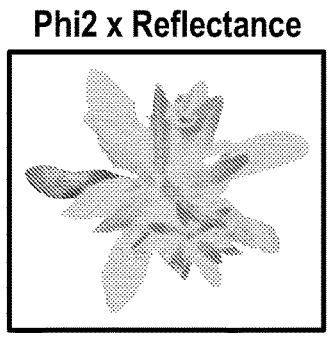
Figure 4D:
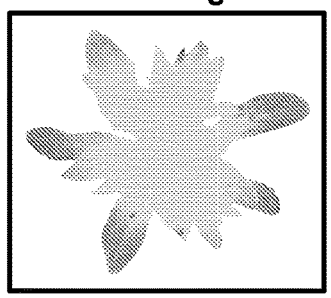
Figure 4E:
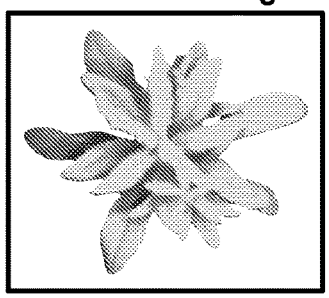
Figure 4F:
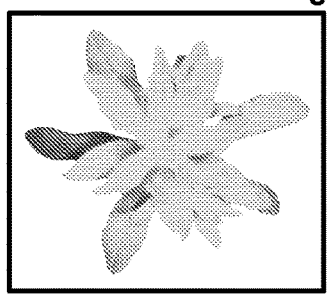
Figure 4A:
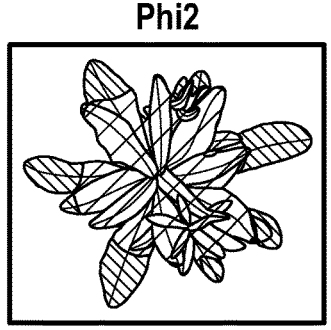
Figure 4B:
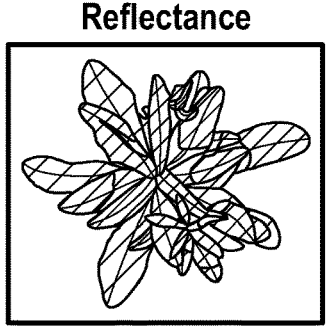
Figure 4C:
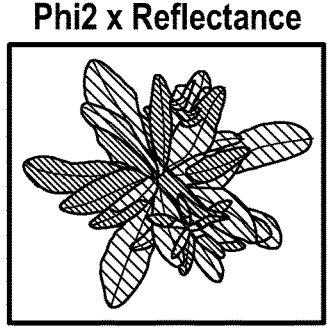
Figure 4D:
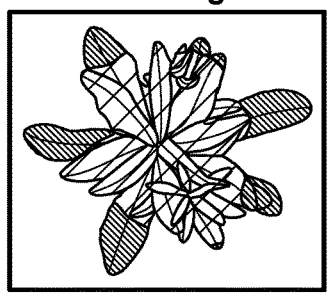
Figure 4E:
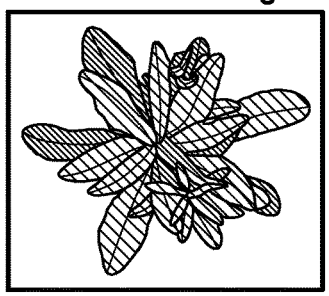
Figure 4F:
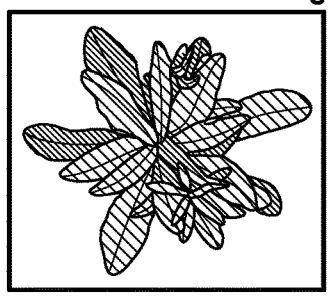

FIGS. 4A and 4B are false color plant images (with black background removed for simplicity), used to estimate photosynthetic electron transfer rate, i.e., efficiency (See FIGS. 4C-4F). FIGS. 4A'-4F' are schematic representations of the images of FIGS. 4A-4F, with the different fills intended to roughly correspond to the different colors obtained with the imaging and modeling. This estimation can be achieved. by multiplying estimates of photochemical efficiency by the rate of absorbed PAR over the entire surface of the plant. Photosynthetic efficiency can be determined by multiplying Phi-2, measured by imaging chlorophyll fluorescence (FIG. 4A) and the IR-reflectance (FIG. 4B), and then comparing Phi-2 image and the IR reflectance image (FIGS. 4A and 4B), with measuring lights that have the same trajectories.

In FIG. 4A, a plant is illuminated from a single direction using a single camera perspective to produce a false-color image primarily orange in the center with yellow to yellow/green on the leaves. The measuring light source can be placed so that it illuminates the plants with light that has the same general angular dependence. In one embodiment, the measuring light source is perpendicular to the ground with a divergence of about 5 to about 15 degrees, such as about 8 to 12 degrees, such as no more or no less than about 10°. Measurements can then be made of Phi-2 fluorescence (FIG. 4A), and the differential reflectance of infrared and PAR light (FIG. 4B) reflecting the amount of light absorbed by the leaf at each pixel position (with color blue representing low levels to color red representing high levels). FIGS. 4C-4F show the calculation of the LEF from the fluorescence-derived images of Phi-2 and reflectance.

As light is known through controlling light or measurement in field conditions, various calculations can be performed using light, reflectance, and Phi-2 fluorescence as shown in the remaining images. For example, the bottom center (FIG. 4E) image shows reflectance multiplied by light, which given a relatively even distribution of light strongly resembles reflectance as shown at top center (FIG. 4B). Reflectance multiplied by Phi-2 fluorescence is shown at top right (FIG. 4C), indicating how photosynthetic efficiency and light distribution overlap. Lastly, the bottom right image (FIG. 4F) shows Phi-2 fluorescence multiplied by reflectance and light intensity, to produce a corrected image of LEF that takes into account uneven distribution of light across the plant canopy. The upper right image shows the simple (current state of the art) image of LEF estimated by multiplying Phi-2 images by the average light intensity, without regard to differences in the degree of light absorption by different plant parts. The bottom right image shows Phi-2 fluorescence multiplied by the estimated light absorbed using the reflectance procedure as described herein, illustrating the fact that the LEF is determined more accurately when the light absorbance is taken into account.

Figures 5A, 5B:
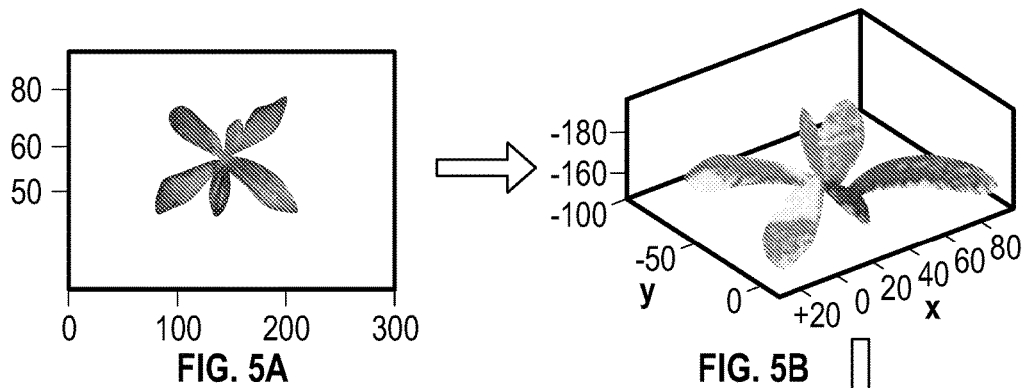
FIGS. 5A-5D show the sequence of steps used to obtain a 3D photosynthesis leaf model according to an embodiment.
Figures 5C, 5D:
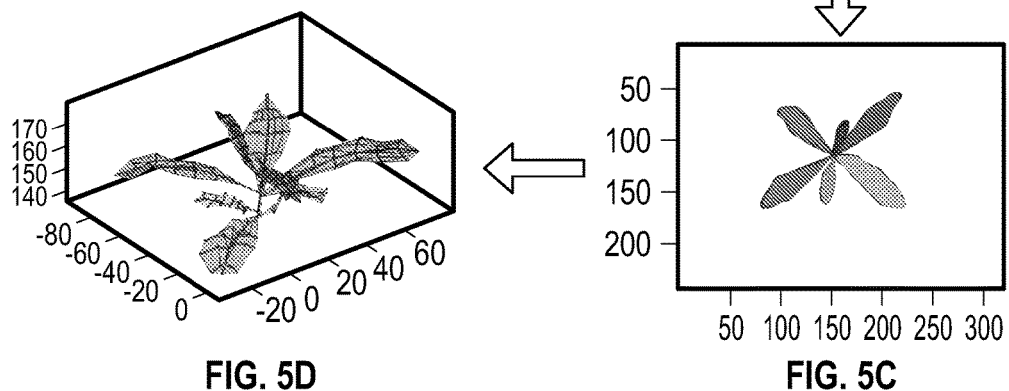
Figures 5A, 5B:
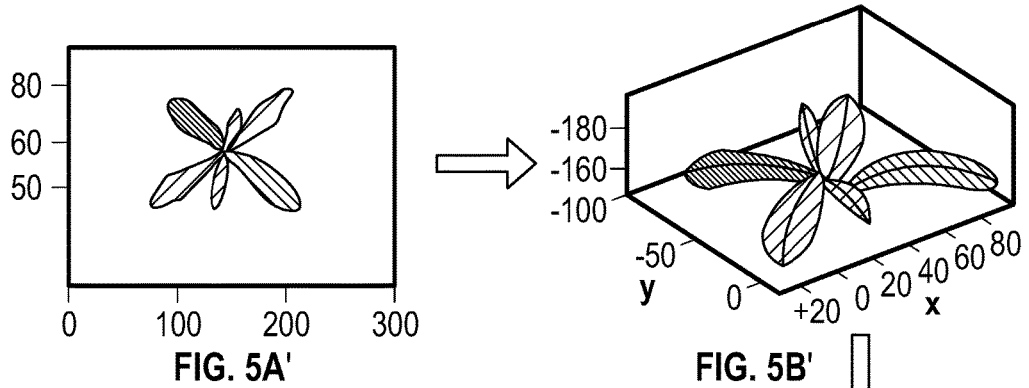
Figures 5C, 5D:
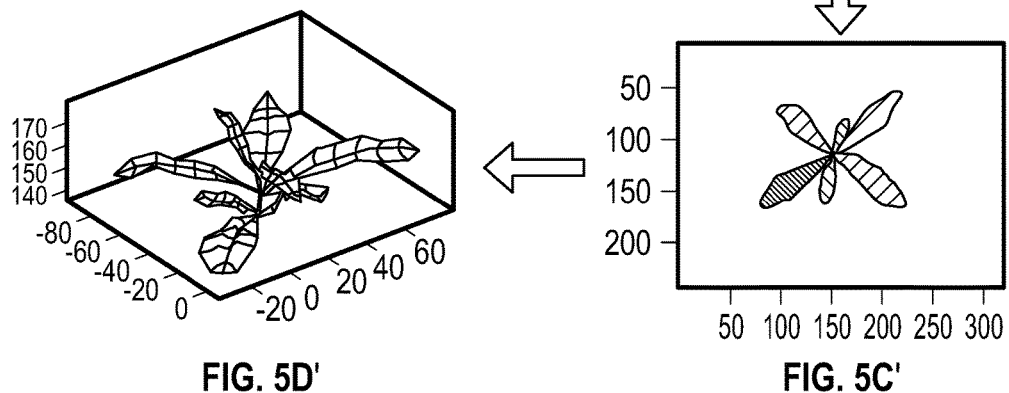

The embodiment in FIGS. 5A-5D shows the steps used to render a three-dimensional leaf model used to estimate photosynthetic efficiency, with FIGS. 5A'-5D' providing a schematic representation of the images in FIG. 5A-5D, with the different fills intended to roughly represent the different colors obtained through the imaging and modeling. FIG. 5A shows depth image of a plant, such as may be employed at 312 of FIG. 3. The depth image (FIG. 5A) is based on two-dimensional imaging, such as infrared imaging of the plant. In one embodiment, the two-dimensional image may be based on a time of flight imaging sensor(s) or other sensor(s) operable to detect position of various points on the surface of the plant leaves. In FIG. 5B, a plot of points on the various plant leaves is presented in three dimension, such that the points on the leaves shown can be processed using software configured to recognize leaf shapes among images and segment images such as the point cloud into individual leaves. The individual leaves are shown in FIG. 5C with a different color representing each distinct leaf. FIG. 5D shows the resulting three-dimensional model of each leaf, including leaf angle and shape, such that surface area and angle of light incidence of each portion of each leaf are modeled. This modeling enables calculation of photosynthetic efficiency based on variations in illuminating light or measured fluorescence, taking into account the angle of each leaf, shading provided by other leaves, and other such factors.

In a more complex example, leaf shapes, angles, and densities can be used to provide other important information about a leaf canopy, such as the efficiency of the canopy at presenting leaves having high photosynthetic efficiency to proper light conditions. Light penetration through such a canopy may be limited to varying degrees, and is further modeled in some complex examples such as by characterizing the light reaching various depths of a canopy or by machine learning algorithms to account for leaf surfaces that are occluded by intervening material in the plant canopy.

Figure 6:
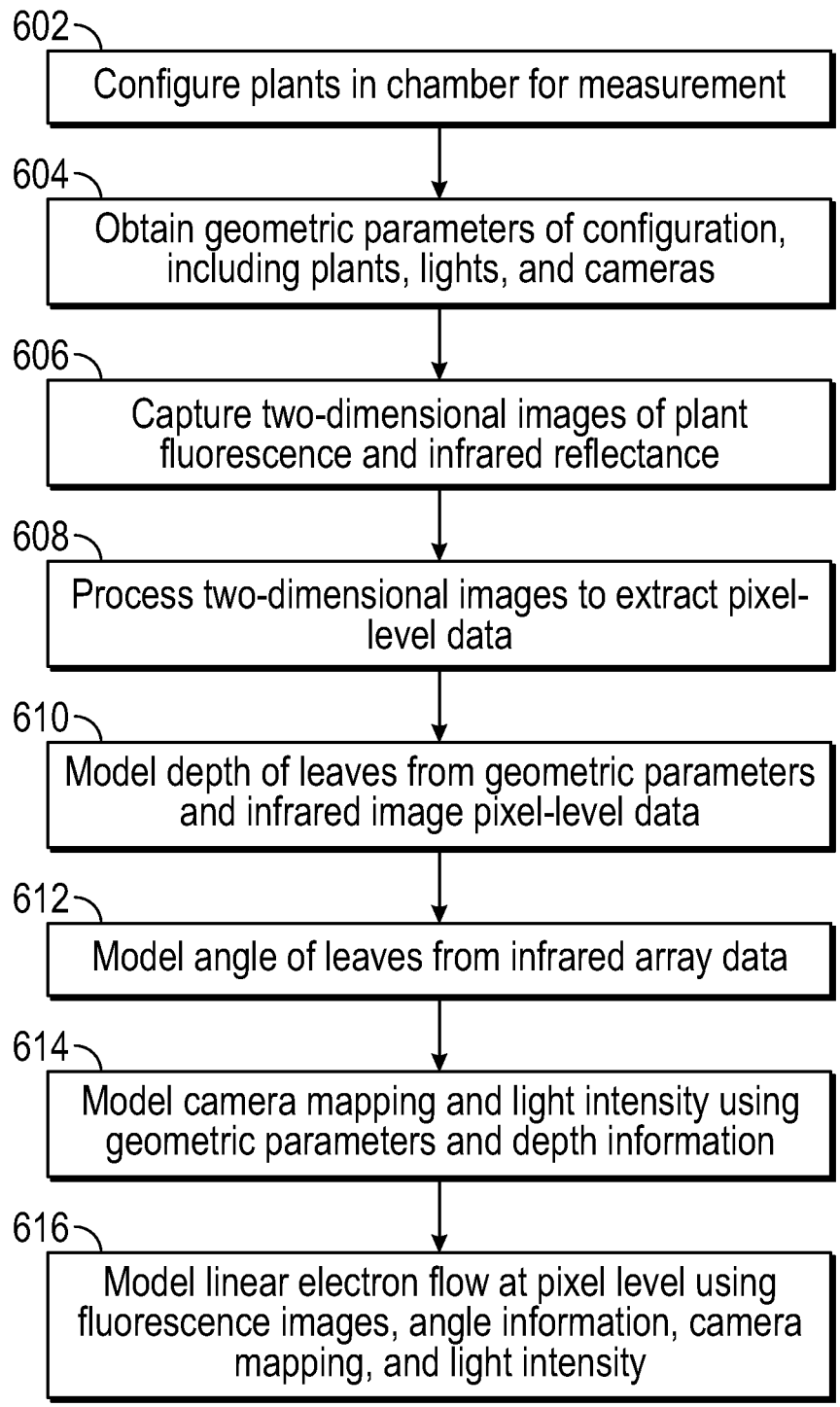
FIG. 6 is a flowchart of a method of estimating the photosynthetic efficiency of plants according to an embodiment.

FIG. 6 is a flowchart of an example method of estimating the photosynthetic efficiency of plants. At 602, plants are set up in the test chamber (such as chamber 102 of FIG. 1) for measurement. In another embodiment, plants are measured in the field, or on location such as in a greenhouse. Next, cameras, lighting, and other geometric configuration information is obtained at 604, including distance from source light to plants, distance from the camera or cameras to the plants, and other such parameters. Two-dimensional images are then captured at 606, including plant fluorescence or Phi-2 images, and infrared reflectance images. In one embodiment, red reflectance images may also captured along with Phi-2 images, and infrared reflectance images. These captured images are processed at 608 to extract pixel-level data of the images, representing the image information captured corresponding to various points on the leaves of the plants. The depth of leaves is then modeled at 610 from geometric parameters determined at 602, and from infrared pixel-level data determined at 608. The angle of leaves is further calculated at 612, based on pixel-level infrared reflectance data determined at 608. A more detailed example of steps 606-612 is shown in FIG. 5.

Next, the light intensity striking each leaf is modeled at 614 using the geometric parameters determined at 604, and the depth information determined at 610. Camera mapping is further calculated at 614 using the geometric parameters determined at 604 and the depth information determined at 610, which includes mapping the images taken at 606 onto the geometric plant leaf models generated at 608-612. The resulting three-dimensional plant leaf model and mapped image data are used to model linear electron flow (LEF) or another characteristic of photosynthesis efficiency at 616, using information including the two-dimensional plant fluorescence image data captured at 606, angle information from 612, leaf geometry modeling from camera mapping at 614, and light intensity information from 614. A more detailed example of 616 is shown in FIG. 3.

The resulting photosynthesis efficiency information is then output, such as being provided as an image having shading or coloring representing the photosynthetic efficiency of the imaged leaves in the plant canopy. Such images enable easy, rapid and more accurate visualization of photosynthetic efficiency of various parts of a plant, and plants having different characteristics such as different genotypes or that have been subject to different environmental conditions.

The method described here results in an efficient and accurate estimate of photosynthetic efficiency of a plant or group of plants, without requiring building a complete three-dimensional model of each plant and its environment. The technique in some examples images the reflectance of plant canopies using infrared (750-940 mm) and/or red (about 635 nm) light having the same optical incident geometry as the actinic light provided to stimulate photosynthesis. The reflectance measurements are analyzed using a fitting equation to estimate the fraction of actinic light absorbed by the leaves. Comparison of reflectance measurements in the red and infrared spectrums can be used to assess the effects of altered chlorophyll content and chloroplast movements.

Photo-induced electron transfer or LEF can be estimated by multiplying Phi-2 (measured by chlorophyll fluorescence imaging) with estimated absorbed light, and output as an image representing linear electron flow using color or tone gradients. Combining data from multiple cameras from multiple angles compensates for variations in leaf movements, growth height, and other such complications that might hinder accuracy in environments where a single optical perspective is used. Further correction for shaded or occluded regions of the plant canopy can be modeled using prior measurements, machine learning algorithms, or other such data to provide more accurate estimates of photosynthesis for the plants, even if such lower layers of leaves are not a part of the three-dimensional model used to characterize efficiency of photosynthesis.

In other embodiments, a single camera or a group of cameras may be swept across a plant canopy, such as by changing the angle of a stationary camera or by moving a camera across a plant canopy to collect images from multiple angles. The distance from the camera to the plant canopy is in some embodiments limited, to preserve high pixel resolution data for the various leaves making up the plant canopy and to facilitate accurate measurement of distance to the plant canopy, angles of the plant leaves, and other such information.

Distance to plant leaves is estimated in some embodiments by use of infrared time-of-flight cameras, or by other suitable means such as laser interferometry. In one embodiment, a camera system such as an Intel Senz 3D infrared time-of-flight camera is used to measure time of flight from the camera to the leaves making up the plant canopy, and optionally a more accurate method such as laser interferometry or other physical measurement is used to verify the camera data.

Although some embodiments presented herein focus on studying differences between various plants, the environmental conditions in which the plants grow may be varied, such that their effect on photosynthesis can be measured or characterized. In one embodiment, wind may be applied to the plant canopy via one or more fans to simulate the effect of leaves fluttering in the wind, as fluttering leaves may have different photosynthetic efficiency characteristics than still leaves. Additionally or alternatively, light conditions may be varied on the seconds or minutes scale to simulate partly cloudy days, such as when clouds pass overhead shading plants but soon blow past restoring direct sunlight.

Figure 7:
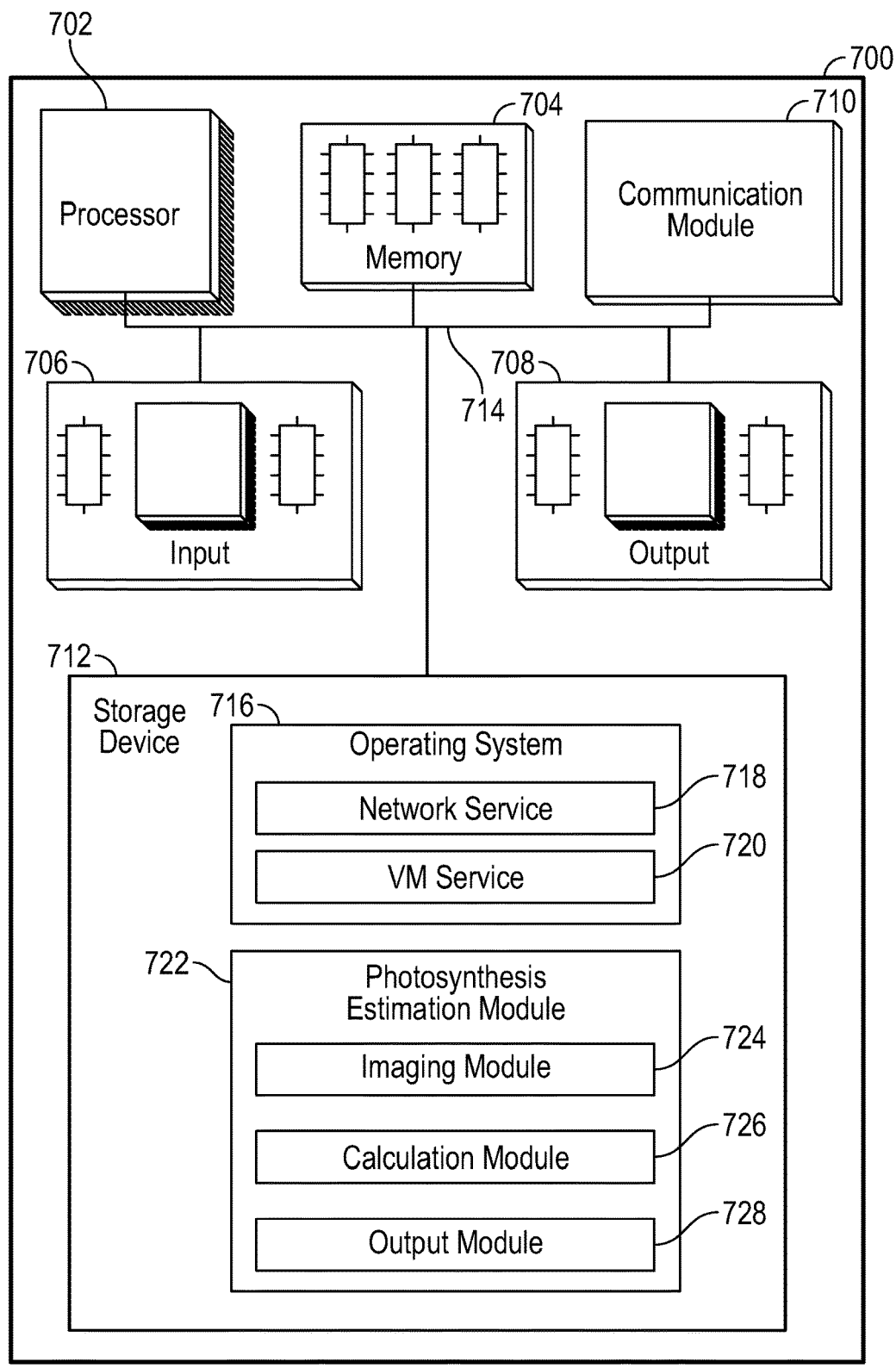
FIG. 7 is a computerized photosynthesis modeling system according to an embodiment.

The methods described herein, such as are illustrated in FIGS. 3 and 6, may be implemented in whole or in part in a computerized system in some embodiments. FIG. 7 shows one embodiment of a computerized photosynthesis modeling system comprising a computing device 700. Although computing device 700 is shown as a standalone computing device, computing device 700 may be any component or system that includes one or more processors or another suitable computing environment useful for executing software instructions, and need not include all of the elements shown here.

In the embodiment shown in FIG. 7, computing device 700 includes one or more processors 702, memory 704, one or more input devices 706, one or more output devices 708, one or more communication modules 710, and one or more storage devices 712. Computing device 700, in one embodiment, further includes an operating system 716 executable by computing device 700. The operating system may include various services, such as a network service 718 and a virtual machine service 720, such as a virtual server. One or more applications, such as photosynthesis estimation module 722 may also be stored on storage device 712, and be executable by computing device 700.

Each of components 702, 704, 706, 708, 710, and 712 may be interconnected (physically, communicatively, and/or operatively) for inter-component communications, such as via one or more communications channels 714. In some embodiments, communication channels 714 include a system bus, network connection, inter-processor communication network, or any other channel for communicating data. Applications such as photosynthesis estimation module 722 and operating system 716 may also communicate information with one another as well as with other components in computing device 700.

In one embodiment, processors 702 are configured to implement functionality and/or process instructions for execution within computing device 700. In one embodiment, processors 702 may be capable of processing instructions stored in storage device 712 or memory 704. In various embodiments, processors 702 may include any one or more of a microprocessor, a controller, a digital signal processor (DSP), an application specific integrated circuit (ASIC), a field-programmable gate array (FPGA), or similar discrete or integrated logic circuitry.

One or more storage devices 712 may be configured to store information within computing device 700 during operation. In one embodiment, storage device 712 is known as a computer-readable storage medium. In various embodiments, storage device 712 comprises temporary memory, meaning that a primary purpose of storage device 712 is not long-term storage. In various embodiments, storage device 712 is a volatile memory, such that storage device 712 does not maintain stored contents when computing device 700 is turned off. In other embodiments, data is loaded from storage device 712 into memory 604 during operation. In various embodiments, volatile memories can include random access memories (RAM), dynamic random access memories (DRAM), static random access memories (SRAM), and other forms of volatile memories known in the art. In one embodiment, storage device 712 is used to store program instructions for execution by processors 702. In other embodiments, storage device 712 and memory 704, are used by software or applications running on computing device 700 such as recommendation module 722 to temporarily store information during program execution.

In various embodiments, storage device 712 includes one or more computer-readable storage media that may be configured to store larger amounts of information than volatile memory. In one embodiment, storage device 712 may further be configured for long-term storage of information. In one embodiment, storage devices 712 include non-volatile storage elements. Examples of such non-volatile storage elements which may be used herein, include, but are not limited to, magnetic hard discs, optical discs, floppy discs, flash memories, or forms of electrically programmable memories (EPROM) or electrically erasable and programmable (EEPROM) memory In various embodiments, computing device 700 also includes one or more communication modules 710. In one embodiment, computing device 700 uses communication module 710 to communicate with external devices via one or more networks, such as one or more wireless networks. In various embodiments, communication module 710 may be a network interface card, such as an Ethernet card, an optical transceiver, a radio frequency transceiver, or any other type of device that can send and/or receive information. Other examples of such network interfaces which may be useful herein include, but are not limited to, Bluetooth, 3G or 4G, WiFi radios, and Near-Field Communications (NFC), and Universal Serial Bus (USB). In various embodiments, computing device 700 uses communication module 610 to wirelessly communicate with an external device such as via a public network.

In one embodiment, computing device 700 also includes one or more input devices 706. In various embodiments, input device 706 is configured to receive input from a user through tactile, audio, or video input. Examples of input device 706 useful herein include, but are not limited to, a touchscreen display, a mouse, a keyboard, a voice responsive system, video camera, microphone or any other type of device for detecting input from a user.

One or more output devices 708 may also be included in computing device 700. In various embodiments, output device 708 is configured to provide output to a user using tactile, audio, or video stimuli. In one embodiment, output device 708 includes, but is not limited to, a display, a sound card, a video graphics adapter card, or any other type of device for converting a signal into an appropriate form understandable to humans or machines. Additional examples of output device 708 useful herein, include, but are not limited to, a speaker, a light-emitting diode (LED) display, a liquid crystal display (LCD), or any other type of device that can generate output to a user.

In one embodiment, computing device 700 includes operating system 716. In various embodiments, operating system 716 controls the operation of components of computing device 700, and provides an interface from various applications such as photosynthesis estimation module 722 to components of computing device 700. In one embodiment, operating system 716 facilitates the communication of various applications such as recommendation module 722 with processors 702, communication unit 710, storage device 712, input device 706, and output device 708. Applications such as photosynthesis estimation module 722 may include, in various embodiments, program instructions and/or data that are executable by computing device 700. In one embodiment, photosynthesis estimation module 722 and its imaging module 724, calculation module 726, and output module 728 may include instructions that cause computing device 700 to perform one or more of the operations and actions described in the examples presented herein.

Any suitable image processing software (hereinafter "software") which can display, edit, analyze, process, save, and optionally print images, such as 8-bit color and grayscale, 16-bit integer, and 32-bit floating point images, can be used. In one embodiment, the software can read multiple types of image file formats, including, but not limited to, TIFF, PNG, GIF, JPEG, BMP, DICOM, and FITS, as well as RAW formats. In one embodiment, the software can support image stacks, i.e., a series of images that share a single window. In one embodiment, the software is multithreaded, so otherwise time-consuming operations can be performed in parallel on hardware having multiple central processing units (CPUs). In one embodiment, the software can calculate area and pixel value statistics of user-defined selections and intensity-thresholded objects. In one embodiment, the software can measure distances and angles. In one embodiment, the software can create density histograms and line profile plots. In one embodiment, the software supports standard image processing functions, such as logical and arithmetical operations between images, contrast manipulation, convolution, Fourier analysis, sharpening, smoothing, edge detection, and median filtering. In one embodiment, the software performs geometric transformations such as scaling, rotation, and flips. In one embodiment, the software supports any number of images simultaneously, limited only by available memory. In one embodiment, ImageJ software, a Java-based image processing program developed at the National Institutes of Health, is used. In one embodiment, the software allows custom acquisition, analysis and processing plugins to be developed using the software's built-in editor and a Java compiler. User-written plugins make it possible to solve many image processing and analysis problems, such as multiple imaging system data comparisons.

The chlorophyll fluorescence profiles or any of the data generated under the varying environments for the test phototrophic organisms may be used to generate databases or data may be compared to other phototrophic organisms and also may be used to generate photosynthetic "signatures."

Reference is now made to the following example, which is offered to further describe various embodiments of the present invention. It should be understood, however, that many variations and modifications may be made while remaining within the scope of the present invention.

EXAMPLE

A single sample of a Camelina plant obtained from the plant growth facilities at Michigan State University Plant Research Lab was placed into a photosystem comparable to photosystem 100 and imaged under 25° C., relative humidity of approximately 65% and illumination conditions described below.

The sample was illuminated under actinic lighting (white Bridgelux BXRA-56C5300 LEDs purchased from Newark Electronics) at a photosynthetically active radiation (PAR) of 300 umol/m$^2$s$^{-1}$. Phi-2 image acquisition was accomplished by arithmetically processing the acquired images to determine Phi-2, based on the relation:

$$Phi\text{-}2 = F'v/F'm = (F'_m - F_s)/F'_m$$

wherein $F'_m$ is the maximum fluorescent yield of a light adapted plant after a saturating pulse; F'v/F'm is the quantum yield of a light adapted plant, Fs is the steady state fluorescence yield of a light adapted plant, no saturating pulse F'v is simply F'm−Fs. A saturating pulse is an intense pulse of actinic light that completely saturates photosystem-II.

The $F_s$ image was captured by adapting the plant under actinic lighting at 300 umol/m$^2$ s$^1$, whereby the actinic light was turned off for approximately 100 μs. During this off-time, the 630 nm measurement light (provided by Luxeon Rebel SMT High Power LEDs Red, LXM2-PD01-0050, Philips Lumiled, San Jose, Calif.) was turned on for approximately 50 μs to induce fluorescence.

The resulting fluorescence was captured with a color-filtered (Schott RG-9 colored glass filter, Edmund Optics) CCD camera (KPV145MC, Hitachi, Chiyoda, Japan Hitachi) (hereinafter "Hitachi camera system") which only accepts the fluorescence or IR-reflectance signal and blocks the measuring light. The F'$_m$ image was captured by exposing the plant to a saturating pulse with an intensity of ~15,000 umol/m$^2$ s$^1$ to completely saturate photosynthesis using actinic light, followed immediately by exposure to an approximately 630 nm measurement light (approximately 50 μs duration), which illuminated the plant to induce fluorescence. The resulting fluorescence was captured with the Hitachi camera system.

The resulting false color images shown in FIGS. 8A and 8B (with the black background removed for simplicity) were operated on arithmetically, using commercially available software (ImageJ Software®), to obtain the resulting (F'$_m$−F$_s$)/F'$_m$→Phi-2 Image (FIG. 8C). FIGS. 8A'-8C' provide schematic representations of the images in FIG. 8A-8C, with the different fills intended to roughly represent the different colors obtained through the imaging and modeling.

To obtain the IR-Reflectance image, the same Camelina plant was exposed to an approximately 940 nm LED light (SFH 4725S, Osram Opto Semiconductors, Inc., Regensburg, Germany) for 50 μs while the Hitachi camera system captured the reflected light.

By weighting the original Phi-2 (LEF) (FIG. 8A) image with an estimate of the incident PAR (IR-Reflectance image, FIG. 8B), the resulting image (FIG. 8C) more accurately shows the relative intensity of LEF. FIG. 8C shows that the amount of LEF is dependent on the amount of light reaching the various locations in the canopy. This light dependent variability is apparent in the resulting Phi-2 (LEF) multiplied by IR-Reflectance image (FIG. 8C), on the right, but not so in the original Phi-2 (LEF) image (FIG. 8A).

In one embodiment, a method of determining photosynthetic characteristics in one or more plants is provided. The method comprising capturing a plurality of images of plant parts in said plants with one or more sensors, wherein the plurality of images comprises a first image comprising measurement of the fluorescence of the plant parts of said plants and a second image comprising capture of reflectance images of the plant parts in said plants upon exposure to a light(s). The method further comprises deriving information regarding a characteristic of photosynthesis of the plant parts of said plants by multiplying the plurality of images.

In one embodiment, the method is provided wherein the multiplying the plurality of images comprises multiplying the first image with the second image.

In one embodiment, the method is provided wherein one of the plurality of images captures absorbance by the plant parts in said plant upon exposure to the light.

In one embodiment, the method is provided wherein the method further comprises capturing additional images wherein the conditions for capturing the additional images are altered relative to the conditions when capturing the first image and the second image.

In one embodiment, the method is provided wherein the conditions are selected from location of the sensors, the number of sensors, a filter on the sensor, the number of the lights provided, the quality of provided light(s), location(s) of the provided light(s) and combinations thereof.

In one embodiment, a method of characterizing photosynthesis in one or more plants is provided. The method comprising capturing a plurality of images of the one or more plants with a sensor, generating a three-dimensional model comprising the plant parts of said plants from the plurality of images, measuring fluorescence of the plant parts of said plants and deriving a characteristic of photosynthesis of said plants using the measured fluorescence of the plant parts of said plants and the three-dimensional model comprising the plant parts of said plants.

In one embodiment, the method is provided wherein the three-dimensional model further comprises one or more geometric parameters, comprising at least one of light position relative to said plants, sensor position relative to said plants, and light position relative to sensor position.

In one embodiment, the method is provided wherein the plurality of images of said plants comprise infrared reflectance images.

In one embodiment, the method is provided further comprising providing infrared light to said plants.

In one embodiment, the method is provided further comprising providing red light to said plants.

In one embodiment, the method is provided wherein measuring fluorescence of the plant parts of said plants comprises removing the provided red light from said plants, and measuring the fluorescence of the plant parts promptly after removing the provided red light.

In one embodiment, the method is provided, where said plants, the sensor, and one or more lights are disposed in a chamber.

In one embodiment, the method is provided, further comprising environmental controls operable to control at least one of temperature, humidity, oxygen, carbon dioxide, and wind in the chamber.

In one embodiment, the method is provided, further comprising one or more instruments operable to measure time of flight from the instrument to the plant parts of said plants.

In one embodiment, the method is provided further comprising compensating for multiple layers of plant parts in said plants in deriving a characteristic of photosynthesis of said plants.

In one embodiment, the method is provided further comprising a computerized system operable to perform the deriving a characteristic of photosynthesis of said plants.

In one embodiment, the method is provided wherein deriving a characteristic of photosynthesis of said plants comprises mapping information from the measured fluorescence of the plant parts of said plants onto the three-dimensional model comprising the plant parts of said plants.

In one embodiment, the method is provided wherein deriving a characteristic of photosynthesis of said plants further comprises mapping a light source illuminating the plant parts of said plants onto the three-dimensional model comprising the plant parts of said plants.

In one embodiment, the method is provided further comprising estimating the light absorbed by the plant parts of said plants by at least one of red light and infrared light reflectance images of the plant parts of said plants, and wherein deriving a characteristic of photosynthesis of said plants further comprises multiplying the measured fluorescence of the plant parts of said plants by the estimated light absorbed by the plant parts of said plants.

In one embodiment, the method is provided wherein the plurality of images of said plants comprise at least one infrared image and at least one red image, and wherein a fraction of actinic light absorbed by the plant parts of said plants is estimated by comparing the infrared and red images.

In one embodiment, the method is provided wherein deriving a characteristic of photosynthesis of said plants comprises mapping a light source illuminating the plant parts of said plants onto the three-dimensional model comprising the plant parts of said plants.

In one embodiment, the method is provided, wherein deriving a characteristic of photosynthesis comprises deriving one or more of a rate of photosynthesis, efficiency of photosynthesis, and linear electron flow (LEF) within the plant parts of said plants.

In one embodiment, the method is provided wherein the one or more sensors comprise one or more cameras and the one or more cameras comprise one or more filters mounted on said cameras.

In one embodiment, the method is provided wherein the plant parts comprises one or more leaves.

In one embodiment, a plant photosynthesis characterization apparatus is provided comprising one or more sensors configured to capture a plurality of images of one or more plants and a computerized system coupled to receive the one or more images of said plants from the one or more sensors, the computerized system operable to generate a three-dimensional model comprising the plant parts of said plants from the received plurality of images, to measure fluorescence of the plant parts of said plants, and to derive a characteristic of photosynthesis of said plants using the measured fluorescence of the plant parts of said plants and the three-dimensional model comprising the plant parts of said plants.

In one embodiment, the apparatus is provided wherein the three-dimensional model further comprises one or more geometric parameters, comprising at least one of light position relative to said plants, sensor position relative to said plants, and light position relative to sensor position.

In one embodiment, the apparatus is provided wherein the one or more sensors comprise infrared sensors and the plurality of images of said plants comprise infrared reflectance images.

In one embodiment, the apparatus is provided further comprising one or more lights operable to provide infrared light to said plants.

In one embodiment, the apparatus is provided further comprising one or more lights operable to provide red light to said plants.

In one embodiment, the apparatus is provided wherein measuring fluorescence of the plant parts of said plants comprises removing the provided red light from said plants by turning off the one or more lights operable to provide red light, and measuring the fluorescence of the plant parts promptly after removing the provided red light.

In one embodiment, the apparatus is provided further comprising a chamber, such that said plants, the sensor, and one or more lights are disposed in the chamber.

In one embodiment, the apparatus is provided further comprising one or more environmental controls operable to control at least one of temperature, humidity, oxygen, carbon dioxide, and wind in the chamber.

In one embodiment, the apparatus is provided further comprising one or more instruments operable to measure time of flight from the instrument to the plant parts of said plants.

In one embodiment, the apparatus is provided comprising the computerized system further operable to compensate for multiple layers of plant parts in said plants in deriving a characteristic of photosynthesis of said plants.

In one embodiment, the apparatus is provided wherein deriving a characteristic of photosynthesis of said plants comprises mapping information from the measured fluorescence of the plant parts of said plants onto the three-dimensional model comprising the plant parts of said plants.

In one embodiment, the apparatus is provided wherein deriving a characteristic of photosynthesis of said plants further comprises mapping a light source illuminating the plant parts of said plants onto the three-dimensional model comprising the plant parts of said plants.

In one embodiment, the apparatus is provided wherein the computerized system further operable to estimate the light absorbed by the plant parts of said plants by at least one of red light and infrared light reflectance images of the plant parts of said plants, and wherein deriving a characteristic of photosynthesis of said plants further comprises multiplying the measured fluorescence of the plant parts of said plants by the estimated light absorbed by the plant parts of said plants.

In one embodiment, the apparatus is provided, wherein the plurality of images of said plants comprise at least one infrared image and at least one red image, and wherein the computerized system is further operable to estimate a fraction of actinic light absorbed by the plant parts of said plants by comparing the infrared and red images.

In one embodiment, the apparatus is provided wherein deriving a characteristic of photosynthesis of said plants comprises mapping a light source illuminating the plant parts of said plants onto the three-dimensional model comprising the plant parts of said plants.

In one embodiment, the apparatus is provided wherein deriving a characteristic of photosynthesis comprises deriving one or more of a rate of photosynthesis, efficiency of photosynthesis, and linear electron flow (LEF) within the plant parts of said plants.

In one embodiment, the apparatus is provided wherein the one or more sensors comprise one or more cameras.

In one embodiment, the apparatus is provided wherein the one or more cameras comprise one or more filters mounted on said cameras.

In one embodiment, the apparatus is provided wherein the plant parts comprises one or more leaves.

In one embodiment, a non-transitory machine-readable medium with instructions stored thereon is provided. In one embodiment, the instructions when executed operable to cause a computerized system to capture a plurality of images of one or more plants via a sensor, to generate a three-dimensional model comprising plant parts of the one or more plants from the plurality of images, to measure fluorescence of the plant parts of said plants and to derive a characteristic of photosynthesis of said plants using the measured fluorescence of the plant parts of said plants and the three-dimensional model comprising the plant parts of said plants.

In one embodiment, the medium is provided wherein the three-dimensional model further comprises one or more geometric parameters, comprising at least one of light position relative to said plants, sensor position relative to said plants, and light position relative to sensor position.

In one embodiment, the medium is provided wherein the plurality of images of said plants comprise infrared reflectance images.

In one embodiment, the medium is provided, the computerized system further operable to control providing infrared light to said plants.

In one embodiment, the medium is provided, wherein the computerized system is further operable to control providing red light to said plants.

In one embodiment, the medium is provided wherein measuring fluorescence of the plant parts of said plants comprises removing the provided red light from said plants, and measuring the fluorescence of the plant parts promptly after removing the provided red light.

In one embodiment, the medium is provided, where said plants, the sensor, and one or more lights are disposed in a chamber.

In one embodiment, the medium is provided, wherein the instructions when executed are further operable to control one or more environmental controls operable to control at least one of temperature, humidity, oxygen, carbon dioxide, and wind in the chamber.

In one embodiment, the medium is provided, wherein the instructions when executed are further operable to control one or more instruments operable to measure time of flight from the instrument to the plant parts of said plants.

In one embodiment, the medium is provided, the instructions when executed further operable to compensate for multiple layers of plant parts in said plants in deriving a characteristic of photosynthesis of said plants.

In one embodiment, the medium is provided, wherein deriving a characteristic of photosynthesis of said plants comprises mapping information from the measured fluorescence of the plant parts of said plants onto the three-dimensional model comprising the plant parts of said plants.

In one embodiment, the medium is provided wherein deriving a characteristic of photosynthesis of said plants further comprises mapping a light source illuminating the plant parts of said plants onto the three-dimensional model comprising the plant parts of said plants.

In one embodiment, the medium is provided, the instructions when executed further operable to estimate the light absorbed by the plant parts of said plants by at least one of red light and infrared light reflectance images of the plant parts of said plants, and wherein deriving a characteristic of photosynthesis of said plants further comprises multiplying the measured fluorescence of the plant parts of said plants by the estimated light absorbed by the plant parts of said plants.

In one embodiment, the medium is provided, wherein the plurality of images of said plants comprise at least one infrared image and at least one red image, and wherein a fraction of actinic light absorbed by the plant parts of said plants is estimated by comparing the infrared and red images.

In one embodiment, the medium is provided, wherein deriving a characteristic of photosynthesis of said plants comprises mapping a light source illuminating the plant parts of said plants onto the three-dimensional model comprising the plant parts of said plants.

In one embodiment, the medium is provided, wherein deriving a characteristic of photosynthesis comprises deriving one or more of a rate of photosynthesis, efficiency of photosynthesis, and linear electron flow (LEF) within the plant parts of said plants.

In one embodiment, the medium is provided wherein the one or more sensors comprise one or more cameras and the one or more cameras comprise one or more filters mounted on said cameras.

In one embodiment, the medium is provided wherein the plant parts comprises one or more leaves.

In one embodiment, a system is provided, the system comprising a controller and a plant photosynthesis characterization apparatus in communication with the controller, wherein the apparatus comprises one or more sensors configured to capture a plurality of images of one or more plants; and a computerized system coupled to receive the one or more images of said plants from the one or more sensors, the computerized system operable to generate a three-dimensional model comprising the plant parts of said plants from the received plurality of images, to measure fluorescence of the plant parts of said plants, and to derive a characteristic of photosynthesis of said plants using the measured fluorescence of the plant parts of said plants and the three-dimensional model comprising the plant parts of said plants.

Although specific embodiments have been illustrated and described herein, any arrangement that achieve the same purpose, structure, or function may be substituted for the specific embodiments shown. This application is intended to cover any adaptations or variations of the embodiments of the invention described herein. These and other embodiments are within the scope of the following claims and their equivalents.

What is claimed is:

1. A method of determining photosynthetic characteristics in one or more plants, comprising:
    capturing a plurality of images of plant parts in said plants with one or more sensors, wherein the plurality of images comprises a first image comprising measurement of the fluorescence of the plant parts and a second image comprising capture of one or more reflectance images of the plant parts upon exposure to one or more lights; and
    deriving information regarding a characteristic of photosynthesis of the plant parts by multiplying the plurality of images.

2. The method of claim 1, wherein one of the plurality of images is used to determine absorbance by the plant parts in said plant upon exposure to the light.

3. The method of claim 1, wherein the method further comprises capturing additional images wherein measuring and/or environmental conditions for capturing the additional images are altered from the measuring and/or environmental conditions for capturing the first image and the second image.

4. The method of claim 3, wherein the measuring conditions are selected from location of said sensors, number of said sensors, presence or absence of a filter on each of said sensors, number of said lights provided, quality of said lights provided, location(s) of said lights provided, and combinations thereof.

5. The method of claim 1, wherein the method further comprises providing infrared and/or red light to the plant parts and capturing the infrared and/or red reflectance images.

6. The method of claim 1, wherein measuring fluorescence of the plant parts comprises providing red light to the plant parts, removing the provided red light from the plant parts, and measuring the fluorescence of the plant parts promptly after removing the provided red light.

7. The method of claim 1, performed in a chamber, wherein the chamber contains one or more sensors, one or more lights, and one or more environmental controls, wherein the method further comprises using said environmental controls to control one or more of temperature, humidity, oxygen, carbon dioxide, and wind in the chamber.

8. The method of claim 1, further comprising one or more instruments, wherein the method further comprises using said instruments to measure time of flight from said instruments to the plant parts.

9. The method of claim 1, further comprising estimating the light absorbed by the plant parts by at least one of red light and infrared light reflectance images of the plant parts, wherein deriving a characteristic of photosynthesis of said plants further comprises multiplying the measured fluorescence of the plant parts by the estimated light absorbed by the plant parts.

10. The method of claim 1, wherein deriving a characteristic of photosynthesis comprises deriving one or more of a rate of photosynthesis, efficiency of photosynthesis, and linear electron flow (LEF) within the plant parts.

11. The method of claim 1, wherein the one or more sensors comprise one or more cameras and the one or more cameras comprise one or more filters mounted on said cameras.

12. The method of claim 1, wherein the plant parts comprise one or more leaves.

13. A method of estimating photosynthesis in a plurality of plants in a plant canopy, comprising:
    capturing a plurality of images of said plants with one or more sensors, wherein said plant canopy is located in a chamber configured to simulate various weather conditions;
    generating a three-dimensional model comprising plant parts of said plants from the plurality of images, wherein the three-dimensional model comprises one or more geometric parameters;
    measuring fluorescence of the plant parts; and
    deriving a characteristic of photosynthesis of the plant parts using the measured fluorescence of the plant parts and the three-dimensional model comprising the plant parts.

14. The method of claim 13, wherein deriving a characteristic of photosynthesis of said plants comprises mapping information from the measured fluorescence of the plant parts onto the three-dimensional model comprising the plant parts.

15. The apparatus of claim 13, wherein said images are captured in the presence of one or more red light sources, infrared light sources, actinic light sources, and/or measurement light sources.

16. A plant photosynthesis characterization apparatus, comprising:
    one or more sensors configured to capture a plurality of images of a plurality of plants in a plant canopy located in a chamber configured to simulate various weather conditions; and
    a computerized system coupled to receive the plurality of images of said plants from said sensors, wherein the computerized system is configured to generate a three-dimensional model of the plant parts from the received plurality of images, to measure fluorescence of the plant parts, and to derive a characteristic of photosynthesis of said plants using the measured fluorescence of the plant parts and the three-dimensional model of the plant parts.

17. The apparatus of claim 16, wherein said images are captured in the presence of one or more light sources selected from red light sources, infrared light sources, actinic light sources, and/or measurement light sources.

18. The apparatus of claim 17, further comprising a chamber, such that said sensors, said light sources, and said environmental controls are configured to control one or more of temperature, humidity, oxygen, carbon dioxide, and wind in the chamber.

19. The apparatus of claim 18, further comprising one or more instruments configured to measure time of flight from the instrument to the plant parts of said plants.

20. The apparatus of claim 19, wherein the computerized system is further configured to compensate for multiple layers of leaves in said plants by deriving a characteristic of photosynthesis of said plants.

21. The apparatus of claim 19, wherein the computerized system is further configured to estimate the light absorbed by the plant parts by at least one of red light and infrared light reflectance images of the plant parts, and the characteristic of photosynthesis derived comprises a multiple of the measured fluorescence of the plant parts with the estimated light absorbed by the plant parts.

22. The apparatus of claim 19, wherein the characteristic of photosynthesis derived comprises one or more of a rate of photosynthesis, efficiency of photosynthesis, and linear electron flow (LEF) within the plant parts.

23. The apparatus of claim 19, wherein said sensors comprise one or more cameras.

24. The apparatus of claim 19, wherein said cameras comprise one or more filters mounted on said cameras.

25. The apparatus of claim 19, wherein said plant parts comprises one or more leaves.

26. A non-transitory machine-readable medium with instructions stored thereon, the instructions when executed operable to cause a computerized system to:
capture a plurality of images of a plurality of plants via one or more sensors in a plant canopy located in a chamber configured to simulate various weather conditions;
generate a three-dimensional model comprising plant parts from the plurality of images;
measure fluorescence of the plant parts; and
derive a characteristic of photosynthesis of said plants using the measured fluorescence of the plant parts and the three-dimensional model comprising the plant parts.

27. The medium of claim 26, wherein the characteristic of photosynthesis derived comprises one or more of a rate of photosynthesis, efficiency of photosynthesis, and linear electron flow (LEF) within the plant parts.

28. The medium of claim 26, wherein said sensors comprise one or more cameras and said cameras have one or more filters mounted thereon.

29. The medium of claim 26, wherein said plant parts comprise one or more leaves.

30. The medium of claim 26, wherein said images are captured in the presence of one or more red light sources, infrared light sources, actinic light sources, and/or measurement light sources.

31. A system comprising:
a controller; and
a plant photosynthesis characterization apparatus in communication with the controller, wherein the apparatus comprises:
one or more sensors configured to capture a plurality of images of a plurality of plants in a plant canopy located in a chamber configured to simulate various weather conditions; and
a computerized system coupled to receive the one or more images of said plants from said sensors, the computerized system configured to generate a three-dimensional model of the plant parts from the received plurality of images, to measure fluorescence of the plant parts, and to derive a characteristic of photosynthesis of said plants using the measured fluorescence of the plant parts and the three-dimensional model comprising the plant parts.

32. The system of claim 31, wherein said images are captured in the presence of one or more red light sources, infrared light sources, actinic light sources, and/or measurement light sources.

33. A plant photosynthesis characterization apparatus, comprising:
one or more sensors configured to capture a plurality of images of a plurality of plants;
a chamber for said sensors, one or more light sources and one or more environmental controls, such that said sensors, said light sources, and said environmental controls are configured to control one or more temperature, humidity, oxygen, carbon dioxide, and wind in the chamber;
one or more instruments configured to measure time of flight from the instrument to the plant parts of said plants; and
a computerized system coupled to receive the plurality of images of said plants from said sensors, wherein the computerized system is configured to generate a three-dimensional model of the plant parts from the received plurality of images, to measure fluorescence of the plant parts, and to derive a characteristic pf photosynthesis of said plants using the measured fluorescence of the plant part and the three-dimensional model of the plant parts, wherein the computerized system is further configured to compensate for multiple layers of leaves in said plants by deriving a characteristic of photosynthesis of said plants.

* * * * *

UNITED STATES PATENT AND TRADEMARK OFFICE
CERTIFICATE OF CORRECTION

PATENT NO. : 10,473,592 B2
APPLICATION NO. : 15/569570
DATED : November 12, 2019
INVENTOR(S) : David Kramer et al.

It is certified that error appears in the above-identified patent and that said Letters Patent is hereby corrected as shown below:

In the Specification

Column 6/Line 49: Error reads as "may be compensated," and should read as "may be compensated for,"

Column 6/Lines 55-56: Error reads as "little of no" and should read as "little or no"

Column 16/Line 46: Error reads as "infra-red" and should read as "infrared"

Column 17/Line 66: Error reads as "quantity of light that leaf 204." and should read as "quantity of light that leaf 204 absorbs."

Column 33/Line 23: Error reads as "any arrangement that achieve" and should read as "any arrangement that achieves"

Signed and Sealed this
Fourteenth Day of January, 2020

Andrei Iancu
*Director of the United States Patent and Trademark Office*